US009006517B2

(12) United States Patent
Bradley et al.

(10) Patent No.: US 9,006,517 B2
(45) Date of Patent: Apr. 14, 2015

(54) METHODS AND COMPOSITIONS FOR PLANT PEST CONTROL

(75) Inventors: John D. Bradley, St. Louis, MO (US); Catherine C. Baublite, Overland, MO (US); Michael J. Crawford, St. Louis, MO (US); Stanislaw Flasinski, Chesterfield, MO (US); Deryck J. Williams, University City, MO (US)

(73) Assignee: Monsanto Technology LLC, St. Louis, MO (US)

( * ) Notice: Subject to any disclaimer, the term of this patent is extended or adjusted under 35 U.S.C. 154(b) by 665 days.

(21) Appl. No.: 12/865,845

(22) PCT Filed: Feb. 9, 2009

(86) PCT No.: PCT/US2009/033560
§ 371 (c)(1),
(2), (4) Date: Nov. 24, 2010

(87) PCT Pub. No.: WO2009/100433
PCT Pub. Date: Aug. 13, 2009

(65) Prior Publication Data
US 2011/0107446 A1 May 5, 2011

Related U.S. Application Data

(60) Provisional application No. 61/027,473, filed on Feb. 10, 2008.

(51) Int. Cl.
*A01H 5/00* (2006.01)
*A01H 5/10* (2006.01)
*A01H 1/00* (2006.01)
*C12N 15/82* (2006.01)
*C12N 15/29* (2006.01)
*A23D 9/00* (2006.01)

(52) U.S. Cl.
CPC ........ *C12N 15/8285* (2013.01); *C12N 15/8286* (2013.01)

(58) Field of Classification Search
None
See application file for complete search history.

(56) References Cited

FOREIGN PATENT DOCUMENTS

WO  WO 03/016551 A2  2/2003
WO  WO 2005/118823 A2  12/2005

OTHER PUBLICATIONS

Chatzivasileiadis et al. 1997. Toxicity of methyl ketones from tomato trichomes to *Tetranychus urticae* Koch. Exper. Appl. Acarology. 21:473-484.*
Gu et al. 2007. Evaluation and identification of potential organic nematicidal volatiles from soil bacteria. Soil Biol. Biochem. 39:2567-2575.*
Guo et al 2004. Protein tolerance to random amino acid change. PNAS. 101(25):9205-9210.*
Flaman et al. 2001. Site-directed mutagenesis of acyl carrier protein (ACP) reveals amino acid residues involved in ACP structure and acyl-ACP synthetase activity. J. Biol. Chem. 276(38):35934-35939.*
Fridman et al. 2005. Metabolic, genomic, and biochemical analyses of glandular trichomes from the wild tomato species *Lycopersicon hirsutum* identify a key enzyme in the biosynthesis of methylketones. Plant Cell. 17:1252-1267.*
Nicolau et al. 2008. Platform biochemicals for a biorenewable chemical industry. Plant J. 54:536-545.*
Van den Broek et al. 1985. Targeting of a foreign protein to chloroplasts by fusion to the transit peptide from the small subunit of ribulose 1,5-bisphosphate carboxylase. Nature. 313:358-363.*
Williams et al. 1980. 2-Tridecanone: A naturally occurring insecticide from the wild tomato *Lycopersicon hirsutum* f. glabratum. Science. 207:888.*
Antonious, "Production and quantification of methyl ketones in wild tomato accessions," *J. Environ. Sci. Health*, B36(6):835-848, 2001.
Fery, "Genetic analysis of 2-tridecanone concentration, leaf trichome characteristics, and tobacco hornworm resistance in tomato," *J. Amer. Soc. Hort. Sci.*, 112(5):886-891, 1987.
Fridman et al., "Metabolic, genomic, and biochemical analyses of glandular trichomes from the wild tomato species *Lycopersicon hirsutum* identify a key enzyme in the biosynthesis of methylketones," *Plant Cell*, 17:1252-1267, 2005.
Fridman et al., "Tomato glandular tichomes as a model system for exploring evolution of specialized metabolism in a single cell," In: Recent Advances in Phytochemistry, Plenum, New York, NY, vol. 40, pp. 115-130, 2006.
GenBank Accession No. AY701574, dated Apr. 9, 2005.
Gu et al., "Evaluation and identification of potential organic nematicidal volatiles from soil bacteria," *Soil Biology & Biochemistry*, 39:2567-2575, 2007.
Hoppmann et al., "The potato granule bound starch synthase chloroplast transit peptide directs recombinant proteins to plastids," *J. Plant Physiol.*, 159:1061-1067, 2002.
Maliepaard et al., "Mapping of QTLs for glandular trichome densities and *Trialeurodes vaporariorum* (greenhouse whitefly) resistance in an F2 from *Lycopersicon esculentum* x *Lycopersicon hirsutum* f. glabratum," *Heredity*, 75:425-433, 1995.
Nienhuis et al., "Restriction fragment length polymorphism analysis of loci associated with insect resistance in tomato," *Crop Sci.*, 27:797-803, 1987.
Wang et al., "Transgenic *Nicotiana tabacum* L. with enhanced trichome exudate cembratrieneols has reduced aphid infestation in the field," *Mol. Breeding*, 13:49-57, 2004.
Wei et al., "Expression and subcellular compartmentation of *Aspergillus niger* β-glucosidase in transgenic tobacco result in an increased insecticidal activity on whiteflies (*Bemisia tabaci*)," *Plant Sci.*, 172:1175-1181, 2007.
Wu et al., "Redirection of cytosolic of plastidic isoprenoid precursors elevates terpene production in plants," *Nature Biotechnology*, 24(11):1441-1447, 2006.

* cited by examiner

*Primary Examiner* — Stuart F Baum
(74) *Attorney, Agent, or Firm* — Dentons US LLP; T. K. Ball Esq.; Carine M. Doyle Esq.

(57) ABSTRACT

The present invention is directed to controlling nematode infestation. The invention discloses methods and compositions for use in controlling nematode infestation by providing recombinant DNA molecules to the cells of a plant in order to achieve a reduction in nematode infestation. The invention is also directed to methods for making transgenic plants that express the recombinant DNA molecule for use in protecting plants from nematode infestation.

34 Claims, No Drawings

SEQUENCE LISTING

<160> NUMBER OF SEQ ID NOS: 62

<210> SEQ ID NO 1
<211> LENGTH: 798
<212> TYPE: DNA
<213> ORGANISM: Artificial sequence

```
<220> FEATURE:
<223> OTHER INFORMATION: Synthetic sequence

<400> SEQUENCE: 1
atggaaaagt ctatgtcacc cttcgtcaag aaacacttcg tgcttgttca tactgctttc     60
cacggtgcct ggtgctggta caagatcgtc gcccttatga aagttcagg ccacaacgtg    120
accgcactgg acctcggggc ctccgggata accccaaac aagctttgca gattcctaac    180
ttcagtgatt atctttctcc acttatggag tttatggcct ctcttcccgc taacgaaaag    240
atcatactcg ttggtcatgc tcttggtggt cttgccattt ctaaagcaat ggaaaccttc    300
cctgagaaaa tatcagtggc tgttttcttg tccggtctta tgcccggacc taatattgac    360
gcaacaaccg tttgtaccaa ggctgggtcc gccgtgttgg ccaactcga caactgcgtg    420
acctacgaaa atggtcctac taatccacct actacccta tcgcaggacc taagtttctc    480
gctacaaacg tgtaccacct ctctccaata gaggatctgg ctcttgccac tgctttggtc    540
aggcctcttt atctgtacct cgctgaggac atatctaaag aagttgtgct ttcttctaag    600
cgttatggtt ccgtgaagcg tgtcttcata gtggcaacag agaatgatgc tcttaagaaa    660
gagtttctca aactgatgat cgagaagaat ccacctgatg aagtgaaaga aattgagggt    720
tctgaccatg ttaccatgat gtcaaagcct caacagttgt ttaccacatt gcttagtata    780
gctaataagt ataaataa                                                  798

<210> SEQ ID NO 2
<211> LENGTH: 798
<212> TYPE: DNA
<213> ORGANISM: artificial sequence
<220> FEATURE:
<223> OTHER INFORMATION: Synthetic sequence

<400> SEQUENCE: 2
atggaaaagt ctatgtcacc cttcgttaag aaacactttg tattggtcca cactgctttc     60
cacggggctt ggtgctggta caagattgtc gcattgatga gatcttccgg tcacaacgtc    120
actgctttgg acctgggagc atctggaatt aaccctaagc aagcattgca aatcccaaac    180
ttcagtgatt acctctctcc tcttatggaa ttcatggcca gccttccagc taacgaaaag    240
atcatcttgg tgggtcacgc ccttggtgga ttggcaatat caaaggccat ggaaacattt    300
ccagaaaaga ttagcgtggc tgtctttctg agtggccttg tgcccggccc taacatcgac    360
gcaactacag tctgcacaaa agctggttcc gctgtattgg acaacttga caattgcgtg    420
acctacgaga atggtcccac taacccaccc accacattga tcgcaggacc taagttcctt    480
gctaccaacg tctaccattt gtctccaatt gaggacttgg ctctggccac cgcacttgtt    540
agacctttgt acctctatct tgcagaagat atttccaagg aagtggtttt gtcttctaaa    600
agatatggtt ctgtgaagag ggtgttcatc gttgccacag agaatgatgc tctgaagaaa    660
gagtttctca aattgatgat tgaaaagaat cctccagacg aagtgaagga gatagaagga    720
agtgaccatg ttactatgat gagtaagcct caacaacttt tcactacact gctgtctatt    780
gcaaacaaat acaagtaa                                                  798

<210> SEQ ID NO 3
<211> LENGTH: 265
<212> TYPE: PRT
<213> ORGANISM: Lycopersicon hirsutum

<400> SEQUENCE: 3
```

```
Met Glu Lys Ser Met Ser Pro Phe Val Lys Lys His Phe Val Leu Val
1               5                   10                  15

His Thr Ala Phe His Gly Ala Trp Cys Trp Tyr Lys Ile Val Ala Leu
                20                  25                  30

Met Arg Ser Ser Gly His Asn Val Thr Ala Leu Asp Leu Gly Ala Ser
            35                  40                  45

Gly Ile Asn Pro Lys Gln Ala Leu Gln Ile Pro Asn Phe Ser Asp Tyr
    50                  55                  60

Leu Ser Pro Leu Met Glu Phe Met Ala Ser Leu Pro Ala Asn Glu Lys
65                  70                  75                  80

Ile Ile Leu Val Gly His Ala Leu Gly Gly Leu Ala Ile Ser Lys Ala
                85                  90                  95

Met Glu Thr Phe Pro Glu Lys Ile Ser Val Ala Val Phe Leu Ser Gly
            100                 105                 110

Leu Met Pro Gly Pro Asn Ile Asp Ala Thr Thr Val Cys Thr Lys Ala
        115                 120                 125

Gly Ser Ala Val Leu Gly Gln Leu Asp Asn Cys Val Thr Tyr Glu Asn
    130                 135                 140

Gly Pro Thr Asn Pro Pro Thr Thr Leu Ile Ala Gly Pro Lys Phe Leu
145                 150                 155                 160

Ala Thr Asn Val Tyr His Leu Ser Pro Ile Glu Asp Leu Ala Leu Ala
                165                 170                 175

Thr Ala Leu Val Arg Pro Leu Tyr Leu Tyr Leu Ala Glu Asp Ile Ser
            180                 185                 190

Lys Glu Val Val Leu Ser Ser Lys Arg Tyr Gly Ser Val Lys Arg Val
    195                 200                 205

Phe Ile Val Ala Thr Glu Asn Asp Ala Leu Lys Lys Glu Phe Leu Lys
210                 215                 220

Leu Met Ile Glu Lys Asn Pro Pro Asp Glu Val Lys Glu Ile Glu Gly
225                 230                 235                 240

Ser Asp His Val Thr Met Met Ser Lys Pro Gln Gln Leu Phe Thr Thr
                245                 250                 255

Leu Leu Ser Ile Ala Asn Lys Tyr Lys
            260                 265
```

<210> SEQ ID NO 4
<211> LENGTH: 801
<212> TYPE: DNA
<213> ORGANISM: Artificial sequence
<220> FEATURE:
<223> OTHER INFORMATION: Synthetic sequence

<400> SEQUENCE: 4

```
atggctgaga agtctatgag tcctttcgtt aagaagcact cgttctagt tcacactgct        60 ttccacggtg cttggtgctg gtacaagatt gttgctttga tgcgtagttc tggtcataac       120
gtgactgctc ttgatctcgg tgctagtggt attaacccaa agcaagcctt gcaaatcccc       180
aactttagcg attacttgtc accactcatg gagtttatgg cctcccttcc tgccaacgag       240
aagatcatac ttgttggaca tgctttagga gggctggcca tctcaaaagc tatggaaacc       300
ttccctgaga gataagcgt ggcagtattt ctctcgggcc tcatgcctgg accaaacatt        360
gacgcaacta ccgtctgtac caaggctgga tctgcagtct tggggcagtt ggataactgc       420 gtgactatg agaatgggcc gacaaatcct ccaacaaccc ttattgccgg acctaagttc       480
ttggcaacga atgtctatca tcttctccc atcgaggatc tggccctcgc tactgctctt       540
```

```
gtccgcccac tttacctcta tctcgctgag acatctcaa aagaagttgt actttcatcc    600
aagagatacg gctccgtgaa gagggttttc attgttgcga cagagaatga tgcacttaag    660
aaagaatttc tgaagctgat gatcgagaag aatccacctg acgaagtgaa agaaatagaa    720
ggctctgacc atgtgactat gatgtccaaa ccacaacagt tgtttacaac gcttttgagt    780
atcgcaaaca agtacaagta a                                              801
```

<210> SEQ ID NO 5
<211> LENGTH: 266
<212> TYPE: PRT
<213> ORGANISM: artificial sequence
<220> FEATURE:
<223> OTHER INFORMATION: Synthetic sequence

<400> SEQUENCE: 5

```
Met Ala Glu Lys Ser Met Ser Pro Phe Val Lys His Phe Val Leu
  1               5                  10                  15

Val His Thr Ala Phe His Gly Ala Trp Cys Trp Tyr Lys Ile Val Ala
                 20                  25                  30

Leu Met Arg Ser Ser Gly His Asn Val Thr Ala Leu Asp Leu Gly Ala
             35                  40                  45

Ser Gly Ile Asn Pro Lys Gln Ala Leu Gln Ile Pro Asn Phe Ser Asp
         50                  55                  60

Tyr Leu Ser Pro Leu Met Glu Phe Met Ala Ser Leu Pro Ala Asn Glu
 65                  70                  75                  80

Lys Ile Ile Leu Val Gly His Ala Leu Gly Gly Leu Ala Ile Ser Lys
                 85                  90                  95

Ala Met Glu Thr Phe Pro Glu Lys Ile Ser Val Ala Val Phe Leu Ser
            100                 105                 110

Gly Leu Met Pro Gly Pro Asn Ile Asp Ala Thr Thr Val Cys Thr Lys
            115                 120                 125

Ala Gly Ser Ala Val Leu Gly Gln Leu Asp Asn Cys Val Thr Tyr Glu
        130                 135                 140

Asn Gly Pro Thr Asn Pro Pro Thr Thr Leu Ile Ala Gly Pro Lys Phe
145                 150                 155                 160

Leu Ala Thr Asn Val Tyr His Leu Ser Pro Ile Glu Asp Leu Ala Leu
                165                 170                 175

Ala Thr Ala Leu Val Arg Pro Leu Tyr Leu Tyr Leu Ala Glu Asp Ile
            180                 185                 190

Ser Lys Glu Val Val Leu Ser Ser Lys Arg Tyr Gly Ser Val Lys Arg
        195                 200                 205

Val Phe Ile Val Ala Thr Glu Asn Asp Ala Leu Lys Lys Glu Phe Leu
210                 215                 220

Lys Leu Met Ile Glu Lys Asn Pro Pro Asp Glu Val Lys Glu Ile Glu
225                 230                 235                 240

Gly Ser Asp His Val Thr Met Met Ser Lys Pro Gln Gln Leu Phe Thr
                245                 250                 255

Thr Leu Leu Ser Ile Ala Asn Lys Tyr Lys
            260                 265
```

<210> SEQ ID NO 6
<211> LENGTH: 801
<212> TYPE: DNA
<213> ORGANISM: Lycopersicon esculentum

<400> SEQUENCE: 6

```
atggctaaga agtctacttc acctttcgtg aagaagcact tcgttctagt tcacactggt    60
ttccacggtg cttggtgctg gtacaagatt gttgctttga tgcgtagttc tggtcacaac   120
gtgactgctc ttgatctagg tgctagtggt attaacccta agcaagccct tgaaatccca   180
catttcagcg actacttgtc cccactcatg gagttcatgg ctagtttgcc ggccaatgag   240
aagataattc ttgtcggtca tgcactcgga ggcttagcca ttagcaaggc tatggagact   300
ttcccagaga aaatttcagt tgccgtattc ctctcaggac ttatgcccgg acctaacatc   360
gacgcaacca cagtttacac taaggcagcg tctgctgtga ttgggcaatt ggacaattac   420
gttacctacg agaacggccc cactaaccca cctactacct taatcgccgg gcctaagttt   480
ctcgctacca atgtttatca tctttccccc atcgaggatc ttgccctggc aacggctctg   540
gtgagacctg tctatctcta tcttgctgag gacatatcca aggaaatcgt actgtcctct   600
aaacgttatg gatctgttaa aagggtcttt attgtggcaa cccagaacga tgctttcaag   660
aaagagtttc tcaaattgat gattgagaaa aatcctccag acgaagtcaa ggagatcgag   720
ggctcagatc atgtgacaat gatgtcaaaa ccacaacagt tgtttacaac attgctgtcg   780
atagcaaata agtacaagtg a                                             801
```

<210> SEQ ID NO 7
<211> LENGTH: 266
<212> TYPE: PRT
<213> ORGANISM: Lycopersicon esculentum

<400> SEQUENCE: 7

```
Met Ala Lys Lys Ser Thr Ser Pro Phe Val Lys Lys His Phe Val Leu
 1               5                  10                  15

Val His Thr Gly Phe His Gly Ala Trp Cys Trp Tyr Lys Ile Val Ala
             20                  25                  30

Leu Met Arg Ser Ser Gly His Asn Val Thr Ala Leu Asp Leu Gly Ala
         35                  40                  45

Ser Gly Ile Asn Pro Lys Gln Ala Leu Glu Ile Pro His Phe Ser Asp
     50                  55                  60

Tyr Leu Ser Pro Leu Met Glu Phe Met Ala Ser Leu Pro Ala Asn Glu
65                  70                  75                  80

Lys Ile Ile Leu Val Gly His Ala Leu Gly Gly Leu Ala Ile Ser Lys
                 85                  90                  95

Ala Met Glu Thr Phe Pro Glu Lys Ile Ser Val Ala Val Phe Leu Ser
            100                 105                 110

Gly Leu Met Pro Gly Pro Asn Ile Asp Ala Thr Thr Val Tyr Thr Lys
        115                 120                 125

Ala Ala Ser Ala Val Ile Gly Gln Leu Asp Asn Tyr Val Thr Tyr Glu
    130                 135                 140

Asn Gly Pro Thr Asn Pro Pro Thr Thr Leu Ile Ala Gly Pro Lys Phe
145                 150                 155                 160

Leu Ala Thr Asn Val Tyr His Leu Ser Pro Ile Glu Asp Leu Ala Leu
                165                 170                 175

Ala Thr Ala Leu Val Arg Pro Val Tyr Leu Tyr Leu Ala Glu Asp Ile
            180                 185                 190

Ser Lys Glu Ile Val Leu Ser Ser Lys Arg Tyr Gly Ser Val Lys Arg
        195                 200                 205

Val Phe Ile Val Ala Thr Gln Asn Asp Ala Phe Lys Lys Glu Phe Leu
    210                 215                 220

Lys Leu Met Ile Glu Lys Asn Pro Pro Asp Glu Val Lys Glu Ile Glu
```

```
                225                 230                 235                 240
Gly Ser Asp His Val Thr Met Met Ser Lys Pro Gln Gln Leu Phe Thr
                    245                 250                 255

Thr Leu Leu Ser Ile Ala Asn Lys Tyr Lys
            260                 265

<210> SEQ ID NO 8
<211> LENGTH: 228
<212> TYPE: DNA
<213> ORGANISM: Arabidopsis thaliana

<400> SEQUENCE: 8
atggcgcaag ttagcagaat ctgcaatggt gtgcagaacc catctcttat ctccaatctc      60
tcgaaatcca gtcaacgcaa atctccctta tcggtttctc tgaagacgca gcagcatcca     120
cgagcttatc cgatttcgtc gtcgtgggga ttgaagaaga gtgggatgac gttaattggc     180
tctgagcttc gtcctcttaa ggtcatgtct tctgtttcca cggcgtgc                 228

<210> SEQ ID NO 9
<211> LENGTH: 76
<212> TYPE: PRT
<213> ORGANISM: Arabidopsis thaliana

<400> SEQUENCE: 9

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys
65                  70                  75

<210> SEQ ID NO 10
<211> LENGTH: 216
<212> TYPE: DNA
<213> ORGANISM: Petunia hybrida

<400> SEQUENCE: 10
atggcccaga tcaacaacat ggcccagggc atccagaccc tgaaccctaa ctctaacttc      60
cacaagccgc aagtgcccaa gtctagctcc ttcctcgtgt tcggctccaa gaagctcaag     120
aatagcgcca attccatgct ggtcctgaag aaagactcga tcttcatgca gaagttctgc     180
tcctttcgca tcagtgcttc ggttgcgact gcctgc                             216

<210> SEQ ID NO 11
<211> LENGTH: 72
<212> TYPE: PRT
<213> ORGANISM: Petunia hybrida

<400> SEQUENCE: 11

Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Ser Phe Leu
            20                  25                  30

Val Phe Gly Ser Lys Lys Leu Lys Asn Ser Ala Asn Ser Met Leu Val
        35                  40                  45
```

Leu Lys Lys Asp Ser Ile Phe Met Gln Lys Phe Cys Ser Phe Arg Ile
    50                  55                  60

Ser Ala Ser Val Ala Thr Ala Cys
65                  70

<210> SEQ ID NO 12
<211> LENGTH: 1026
<212> TYPE: DNA
<213> ORGANISM: artificial sequence
<220> FEATURE:
<223> OTHER INFORMATION: Synthetic sequence

<400> SEQUENCE: 12

```
atggcgcaag ttagcagaat ctgcaatggt gtgcagaacc catctcttat ctccaatctc      60
tcgaaatcca gtcaacgcaa atctccctta tcggtttctc tgaagacgca gcagcatcca     120
cgagcttatc cgatttcgtc gtcgtgggga ttgaagaaga gtgggatgac gttaattggc     180
tctgagcttc gtcctcttaa ggtcatgtct tctgtttcca cggcgtgcat ggaaaagtct     240
atgtcaccct tcgtcaagaa acacttcgtg cttgttcata ctgctttcca cggtgcctgg     300
tgctggtaca agatcgtcgc ccttatgaga agttcaggcc acaacgtgac cgcactggac     360
ctcggggcct ccgggataaa ccccaaacaa gctttgcaga ttcctaactt cagtgattat     420
ctttctccac ttatggagtt tatggcctct cttcccgcta acgaaaagat catactcgtt     480
ggtcatgctc ttggtggtct tgccatttct aaagcaatgg aaaccttccc tgagaaaata     540
tcagtggctg ttttcttgtc cggtcttatg cccggaccta atattgacgc aacaaccgtt     600
tgtaccaagg ctgggtccgc cgtgttgggc caactcgaca actgcgtgac ctacgaaaat     660
ggtcctacta atccacctac tacccttatc gcaggaccta gtttctcgc tacaaacgtg     720
taccacctct ctccaataga ggatctggct cttgccactg ctttggtcag gcctctttat     780
ctgtacctcg ctgaggacat atctaaagaa gttgtgcttt cttctaagcg ttatggttcc     840
gtgaagcgtg tcttcatagt ggcaacagag aatgatgctc ttaagaaaga gtttctcaaa     900
ctgatgatcg agaagaatcc acctgatgaa gtgaaagaaa ttgagggttc tgaccatgtt     960
accatgatgt caaagcctca acagttgttt accacattgc ttagtatagc taataagtat    1020
aaataa                                                               1026
```

<210> SEQ ID NO 13
<211> LENGTH: 341
<212> TYPE: PRT
<213> ORGANISM: artificial sequence
<220> FEATURE:
<223> OTHER INFORMATION: Synthetic sequence

<400> SEQUENCE: 13

Met Ala Gln Val Ser Arg Ile Cys Asn Gly Val Gln Asn Pro Ser Leu
1               5                   10                  15

Ile Ser Asn Leu Ser Lys Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys Met Glu Lys Ser
65                  70                  75                  80

Met Ser Pro Phe Val Lys Lys His Phe Val Leu Val His Thr Ala Phe

```
            85                  90                  95
His Gly Ala Trp Cys Trp Tyr Lys Ile Val Ala Leu Met Arg Ser Ser
            100                 105                 110

Gly His Asn Val Thr Ala Leu Asp Leu Gly Ala Ser Gly Ile Asn Pro
            115                 120                 125

Lys Gln Ala Leu Gln Ile Pro Asn Phe Ser Asp Tyr Leu Ser Pro Leu
            130                 135                 140

Met Glu Phe Met Ala Ser Leu Pro Ala Asn Glu Lys Ile Ile Leu Val
145                 150                 155                 160

Gly His Ala Leu Gly Gly Leu Ala Ile Ser Lys Ala Met Glu Thr Phe
            165                 170                 175

Pro Glu Lys Ile Ser Val Ala Val Phe Leu Ser Gly Leu Met Pro Gly
            180                 185                 190

Pro Asn Ile Asp Ala Thr Thr Val Cys Thr Lys Ala Gly Ser Ala Val
            195                 200                 205

Leu Gly Gln Leu Asp Asn Cys Val Thr Tyr Glu Asn Gly Pro Thr Asn
            210                 215                 220

Pro Pro Thr Thr Leu Ile Ala Gly Pro Lys Phe Leu Ala Thr Asn Val
225                 230                 235                 240

Tyr His Leu Ser Pro Ile Glu Asp Leu Ala Leu Ala Thr Ala Leu Val
            245                 250                 255

Arg Pro Leu Tyr Leu Tyr Leu Ala Glu Asp Ile Ser Lys Glu Val Val
            260                 265                 270

Leu Ser Ser Lys Arg Tyr Gly Ser Val Lys Arg Val Phe Ile Val Ala
            275                 280                 285

Thr Glu Asn Asp Ala Leu Lys Lys Glu Phe Leu Lys Leu Met Ile Glu
            290                 295                 300

Lys Asn Pro Pro Asp Glu Val Lys Glu Ile Glu Gly Ser Asp His Val
305                 310                 315                 320

Thr Met Met Ser Lys Pro Gln Gln Leu Phe Thr Thr Leu Leu Ser Ile
            325                 330                 335

Ala Asn Lys Tyr Lys
            340

<210> SEQ ID NO 14
<211> LENGTH: 1014
<212> TYPE: DNA
<213> ORGANISM: artificial sequence
<220> FEATURE:
<223> OTHER INFORMATION: Synthetic sequence

<400> SEQUENCE: 14
atggcccaga tcaacaacat ggcccagggc atccagaccc tgaaccctaa ctctaacttc    60
cacaagccgc aagtgcccaa gtctagctcc ttcctcgtgt tcggctccaa gaagctcaag   120
aatagcgcca attccatgct ggtcctgaag aaagactcga tcttcatgca gaagttctgc   180
tcctttcgca tcagtgcttc ggttgcgact gcctgcatgg aaaagtctat gtcacccttc   240
gtcaagaaac acttcgtgct tgttcatact gctttccacg gtgcctggtg ctggtacaag   300
atcgtcgccc ttatgagaag ttcaggccac aacgtgaccg cactggacct cggggcctcc   360 gggataaaacc ccaaacaagc tttgcagatt cctaacttca gtgattatct ttctccactt   420
atggagttta tggcctctct tcccgctaac gaaaagatca tactcgttgg tcatgctctt   480
ggtggtcttg ccatttctaa agcaatggaa accttccctg agaaaatatc agtggctgtt   540
ttccttgtcc gtcttatgcc cggacctaat attgacgcaa caccgtttg taccaaggct   600
```

```
gggtccgccg tgttgggcca actcgacaac tgcgtgacct acgaaaatgg tcctactaat    660
ccacctacta cccttatcgc aggacctaag tttctcgcta caaacgtgta ccacctctct    720
ccaatagagg atctggctct tgccactgct ttggtcaggc ctctttatct gtacctcgct    780
gaggacatat ctaaagaagt tgtgctttct tctaagcgtt atggttccgt gaagcgtgtc    840
ttcatagtgg caacagagaa tgatgctctt aagaaagagt ttctcaaact gatgatcgag    900
aagaatccac ctgatgaagt gaaagaaatt gagggttctg accatgttac catgatgtca    960
aagcctcaac agttgtttac cacattgctt agtatagcta ataagtataa ataa         1014
```

<210> SEQ ID NO 15
<211> LENGTH: 337
<212> TYPE: PRT
<213> ORGANISM: artificial sequence
<220> FEATURE:
<223> OTHER INFORMATION: Synthetic sequence

<400> SEQUENCE: 15

```
Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Phe Leu
            20                  25                  30

Val Phe Gly Ser Lys Lys Leu Lys Asn Ser Ala Asn Ser Met Leu Val
        35                  40                  45

Leu Lys Lys Asp Ser Ile Phe Met Gln Lys Phe Cys Ser Phe Arg Ile
    50                  55                  60

Ser Ala Ser Val Ala Thr Ala Cys Met Glu Lys Ser Met Ser Pro Phe
65                  70                  75                  80

Val Lys Lys His Phe Val Leu Val His Thr Ala Phe His Gly Ala Trp
                85                  90                  95

Cys Trp Tyr Lys Ile Val Ala Leu Met Arg Ser Ser Gly His Asn Val
            100                 105                 110

Thr Ala Leu Asp Leu Gly Ala Ser Gly Ile Asn Pro Lys Gln Ala Leu
        115                 120                 125

Gln Ile Pro Asn Phe Ser Asp Tyr Leu Ser Pro Leu Met Glu Phe Met
    130                 135                 140

Ala Ser Leu Pro Ala Asn Glu Lys Ile Ile Leu Val Gly His Ala Leu
145                 150                 155                 160

Gly Gly Leu Ala Ile Ser Lys Ala Met Glu Thr Phe Pro Glu Lys Ile
                165                 170                 175

Ser Val Ala Val Phe Leu Ser Gly Leu Met Pro Gly Pro Asn Ile Asp
            180                 185                 190

Ala Thr Thr Val Cys Thr Lys Ala Gly Ser Ala Val Leu Gly Gln Leu
        195                 200                 205

Asp Asn Cys Val Thr Tyr Glu Asn Gly Pro Thr Asn Pro Pro Thr Thr
    210                 215                 220

Leu Ile Ala Gly Pro Lys Phe Leu Ala Thr Asn Val Tyr His Leu Ser
225                 230                 235                 240

Pro Ile Glu Asp Leu Ala Leu Ala Thr Ala Leu Val Arg Pro Leu Tyr
                245                 250                 255

Leu Tyr Leu Ala Glu Asp Ile Ser Lys Glu Val Val Leu Ser Ser Lys
            260                 265                 270

Arg Tyr Gly Ser Val Lys Arg Val Phe Ile Val Ala Thr Glu Asn Asp
        275                 280                 285
```

```
Ala Leu Lys Lys Glu Phe Leu Lys Leu Met Ile Glu Lys Asn Pro Pro
    290                 295                 300

Asp Glu Val Lys Glu Ile Glu Gly Ser Asp His Val Thr Met Met Ser
305                 310                 315                 320

Lys Pro Gln Gln Leu Phe Thr Thr Leu Leu Ser Ile Ala Asn Lys Tyr
                325                 330                 335

Lys

<210> SEQ ID NO 16
<211> LENGTH: 1026
<212> TYPE: DNA
<213> ORGANISM: artificial sequence
<220> FEATURE:
<223> OTHER INFORMATION: Synthetic sequence

<400> SEQUENCE: 16
atggcgcaag ttagcagaat ctgcaatggt gtgcagaacc catctcttat ctccaatctc      60
tcgaaatcca gtaacgcaa atctccctta tcggtttctc tgaagacgca gcagcatcca     120
cgagcttatc cgatttcgtc gtcgtgggga ttgaagaaga gtgggatgac gttaattggc     180
tctgagcttc gtcctcttaa ggtcatgtct tctgtttcca cggcgtgcat ggaaaagtct     240
atgtcaccct tcgttaagaa acactttgta ttggtccaca ctgctttcca cggggcttgg     300
tgctggtaca agattgtcgc attgatgaga tcttccggtc acaacgtcac tgctttggac     360
ctgggagcat ctggaattaa ccctaagcaa gcattgcaaa tcccaaactt cagtgattac     420
ctctctcctc ttatggaatt catggccagc cttccagcta acgaaaagat catcttggtg     480
ggtcacgccc ttggtggatt ggcaatatca aaggccatgg aaacatttcc agaaaagatt     540
agcgtggctg tctttctgag tggccttatg cccggcccta acatcgacgc aactacagtc     600
tgcacaaaag ctggttccgc tgtattggga caacttgaca attgcgtgac ctacgagaat     660
ggtcccacta acccacccac acattgatc gcaggaccta gttccttgc taccaacgtc     720 taccatttgt ctccaattga ggacttggct ctggccaccg cacttgttag acctttgtac     780
ctctatcttg cagaagatat ttccaaggaa gtggttttgt cttctaaaag atatggttct     840
gtgaagaggg tgttcatcgt tgccacagag aatgatgctc tgaagaaaga gtttctcaaa     900
ttgatgattg aaaagaatcc tccagacgaa gtgaaggaga tagaaggaag tgaccatgtt     960
actatgatga gtaagcctca acaactttc actacactgc tgtctattgc aaacaaatac    1020
aagtaa                                                               1026

<210> SEQ ID NO 17
<211> LENGTH: 341
<212> TYPE: PRT
<213> ORGANISM: artificial sequence
<220> FEATURE:
<223> OTHER INFORMATION: Synthetic sequence

<400> SEQUENCE: 17

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
                20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
        50                  55                  60
```

```
Pro Leu Lys Val Met Ser Val Ser Thr Ala Cys Met Glu Lys Ser
 65                  70                  75                  80

Met Ser Pro Phe Val Lys Lys His Phe Val Leu Val His Thr Ala Phe
                 85                  90                  95

His Gly Ala Trp Cys Trp Tyr Lys Ile Val Ala Leu Met Arg Ser Ser
            100                 105                 110

Gly His Asn Val Thr Ala Leu Asp Leu Gly Ala Ser Gly Ile Asn Pro
        115                 120                 125

Lys Gln Ala Leu Gln Ile Pro Asn Phe Ser Asp Tyr Leu Ser Pro Leu
    130                 135                 140

Met Glu Phe Met Ala Ser Leu Pro Ala Asn Glu Lys Ile Ile Leu Val
145                 150                 155                 160

Gly His Ala Leu Gly Gly Leu Ala Ile Ser Lys Ala Met Glu Thr Phe
                165                 170                 175

Pro Glu Lys Ile Ser Val Ala Val Phe Leu Ser Gly Leu Met Pro Gly
            180                 185                 190

Pro Asn Ile Asp Ala Thr Thr Val Cys Thr Lys Ala Gly Ser Ala Val
        195                 200                 205

Leu Gly Gln Leu Asp Asn Cys Val Thr Tyr Glu Asn Gly Pro Thr Asn
    210                 215                 220

Pro Pro Thr Thr Leu Ile Ala Gly Pro Lys Phe Leu Ala Thr Asn Val
225                 230                 235                 240

Tyr His Leu Ser Pro Ile Glu Asp Leu Ala Leu Ala Thr Ala Leu Val
                245                 250                 255

Arg Pro Leu Tyr Leu Tyr Leu Ala Glu Asp Ile Ser Lys Glu Val Val
            260                 265                 270

Leu Ser Ser Lys Arg Tyr Gly Ser Val Lys Arg Val Phe Ile Val Ala
        275                 280                 285

Thr Glu Asn Asp Ala Leu Lys Lys Glu Phe Leu Lys Leu Met Ile Glu
    290                 295                 300

Lys Asn Pro Pro Asp Glu Val Lys Glu Ile Glu Gly Ser Asp His Val
305                 310                 315                 320

Thr Met Met Ser Lys Pro Gln Gln Leu Phe Thr Thr Leu Leu Ser Ile
                325                 330                 335

Ala Asn Lys Tyr Lys
            340

<210> SEQ ID NO 18
<211> LENGTH: 1014
<212> TYPE: DNA
<213> ORGANISM: artificial sequence
<220> FEATURE:
<223> OTHER INFORMATION: Synthetic sequence

<400> SEQUENCE: 18
atggcccaga tcaacaacat ggcccagggc atccagaccc tgaaccctaa ctctaacttc      60
cacaagccgc aagtgcccaa gtctagctcc ttcctcgtgt tcggctccaa gaagctcaag     120
aatagcgcca attccatgct ggtcctgaag aaagactcga tcttcatgca agagttctgc     180
tcctttcgca tcagtgcttc ggttgcgact gcctgcatgg aaaagtctat gtcacccttc     240
gttaagaaac actttgtatt ggtccacact gctttccacg ggcttggtg ctggtacaag      300 attgtcgcat tgatgagatc ttccggtcac aacgtcactg ctttggacct gggagcatct     360
ggaattaacc ctaagcaagc attgcaaatc ccaaacttca gtgattacct ctctcctctt     420
atggaattca tggccagcct tccagctaac gaaaagatca tcttggtggg tcacgccctt     480
```

-continued

```
ggtggattgg caatatcaaa ggccatggaa acatttccag aaaagattag cgtggctgtc      540
tttctgagtg gccttatgcc cggccctaac atcgacgcaa ctacagtctg cacaaaagct      600
ggttccgctg tattgggaca acttgacaat tgcgtgacct acgagaatgg tcccactaac      660
ccacccacca cattgatcgc aggacctaag ttccttgcta ccaacgtcta ccatttgtct      720
ccaattgagg acttggctct ggccaccgca cttgttagac cttgtacct ctatcttgca      780 gaagatattt ccaaggaagt ggttttgtct tctaaaagat atggttctgt gaagagggtg      840
ttcatcgttg ccacagagaa tgatgctctg aagaaagagt ttctcaaatt gatgattgaa      900
aagaatcctc cagacgaagt gaaggagata gaaggaagtg accatgttac tatgatgagt      960
aagcctcaac aacttttcac tacactgctg tctattgcaa acaaatacaa gtaa           1014
```

<210> SEQ ID NO 19
<211> LENGTH: 337
<212> TYPE: PRT
<213> ORGANISM: artificial sequence
<220> FEATURE:
<223> OTHER INFORMATION: Synthetic sequence

<400> SEQUENCE: 19

```
Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Ser Phe Leu
            20                  25                  30

Val Phe Gly Ser Lys Lys Leu Lys Asn Ser Ala Asn Ser Met Leu Val
        35                  40                  45

Leu Lys Lys Asp Ser Ile Phe Met Gln Lys Phe Cys Ser Phe Arg Ile
    50                  55                  60

Ser Ala Ser Val Ala Thr Ala Cys Met Glu Lys Ser Met Ser Pro Phe
65                  70                  75                  80

Val Lys Lys His Phe Val Leu Val His Thr Ala Phe His Gly Ala Trp
                85                  90                  95

Cys Trp Tyr Lys Ile Val Ala Leu Met Arg Ser Ser Gly His Asn Val
            100                 105                 110

Thr Ala Leu Asp Leu Gly Ala Ser Gly Ile Asn Pro Lys Gln Ala Leu
        115                 120                 125

Gln Ile Pro Asn Phe Ser Asp Tyr Leu Ser Pro Leu Met Glu Phe Met
    130                 135                 140

Ala Ser Leu Pro Ala Asn Glu Lys Ile Ile Leu Val Gly His Ala Leu
145                 150                 155                 160

Gly Gly Leu Ala Ile Ser Lys Ala Met Glu Thr Phe Pro Glu Lys Ile
                165                 170                 175

Ser Val Ala Val Phe Leu Ser Gly Leu Met Pro Gly Pro Asn Ile Asp
            180                 185                 190

Ala Thr Thr Val Cys Thr Lys Ala Gly Ser Ala Val Leu Gly Gln Leu
        195                 200                 205

Asp Asn Cys Val Thr Tyr Glu Asn Gly Pro Thr Asn Pro Thr Thr
    210                 215                 220

Leu Ile Ala Gly Pro Lys Phe Leu Ala Thr Asn Val Tyr His Leu Ser
225                 230                 235                 240

Pro Ile Glu Asp Leu Ala Leu Ala Thr Ala Leu Val Arg Pro Leu Tyr
                245                 250                 255

Leu Tyr Leu Ala Glu Asp Ile Ser Lys Glu Val Val Leu Ser Ser Lys
            260                 265                 270
```

```
Arg Tyr Gly Ser Val Lys Arg Val Phe Ile Val Ala Thr Glu Asn Asp
            275                 280                 285

Ala Leu Lys Lys Glu Phe Leu Lys Leu Met Ile Glu Lys Asn Pro Pro
    290                 295                 300

Asp Glu Val Lys Glu Ile Glu Gly Ser Asp His Val Thr Met Met Ser
305                 310                 315                 320

Lys Pro Gln Gln Leu Phe Thr Thr Leu Leu Ser Ile Ala Asn Lys Tyr
                325                 330                 335

Lys

<210> SEQ ID NO 20
<211> LENGTH: 1029
<212> TYPE: DNA
<213> ORGANISM: artificial sequence
<220> FEATURE:
<223> OTHER INFORMATION: Synthetic sequence

<400> SEQUENCE: 20
atggcgcaag ttagcagaat ctgcaatggt gtgcagaacc catctcttat ctccaatctc      60
tcgaaatcca gtcaacgcaa atctcccttt tcggtttctc tgaagacgca gcagcatcca     120
cgagcttatc cgatttcgtc gtcgtgggga ttgaagaaga gtgggatgac gttaattggc     180
tctgagcttc gtcctcttaa ggtcatgtct ctgtttcca cggcgtgcat ggctgagaag      240
tctatgagtc ctttcgttaa gaagcacttc gttctagttc acactgcttt ccacggtgct     300
tggtgctggt acaagattgt tgctttgatg cgtagttctg gtcataacgt gactgctctt     360
gatctcggtg ctagtggtat taacccaaag caagccttgc aaatccccaa ctttagcgat     420
tacttgtcac cactcatgga gtttatggcc tcccttcctg ccaacgagaa gatcatactt     480
gttggacatg ctttaggagg gctggccatc tcaaaagcta tggaaacctt ccctgagaag     540
ataagcgtgg cagtatttct ctcgggcctc atgcctggac aaacattga cgcaactacc     600 gtctgtacca aggctggatc tgcagtcttg ggcagttgg ataactgcgt gacttatgag      660
aatgggccga caatcctcc aacaacccct attgccggac taagttctt ggcaacgaat      720 gtctatcatc tttctcccat cgaggatctg gccctcgcta ctgctcttgt ccgcccactt     780
tacctctatc tcgctgagga catctcaaaa gaagttgtac tttcatccaa gagatacggc     840
tccgtgaaga gggttttcat tgttgcgaca gagaatgatg cacttaagaa agaatttctg     900
aagctgatga tcgagaagaa tccacctgac gaagtgaaag aaatagaagg ctctgaccat     960
gtgactatga tgtccaaacc acaacagttg tttacaacgc ttttgagtat cgcaaacaag    1020
tacaagtaa                                                            1029

<210> SEQ ID NO 21
<211> LENGTH: 342
<212> TYPE: PRT
<213> ORGANISM: artificial sequence
<220> FEATURE:
<223> OTHER INFORMATION: Synthetic sequence

<400> SEQUENCE: 21

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45
```

```
Trp Gly Leu Lys Lys Ser Gly Met Thr Leu Ile Gly Ser Glu Leu Arg
 50                  55                  60

Pro Leu Lys Val Met Ser Val Ser Thr Ala Cys Met Ala Glu Lys
65                  70                  75                  80

Ser Met Ser Pro Phe Val Lys Lys His Phe Val Leu Val His Thr Ala
                85                  90                  95

Phe His Gly Ala Trp Cys Trp Tyr Lys Ile Val Ala Leu Met Arg Ser
                100                 105                 110

Ser Gly His Asn Val Thr Ala Leu Asp Leu Gly Ala Ser Gly Ile Asn
                115                 120                 125

Pro Lys Gln Ala Leu Gln Ile Pro Asn Phe Ser Asp Tyr Leu Ser Pro
            130                 135                 140

Leu Met Glu Phe Met Ala Ser Leu Pro Ala Asn Glu Lys Ile Ile Leu
145                 150                 155                 160

Val Gly His Ala Leu Gly Gly Leu Ala Ile Ser Lys Ala Met Glu Thr
                165                 170                 175

Phe Pro Glu Lys Ile Ser Val Ala Val Phe Leu Ser Gly Leu Met Pro
                180                 185                 190

Gly Pro Asn Ile Asp Ala Thr Thr Val Cys Thr Lys Ala Gly Ser Ala
            195                 200                 205

Val Leu Gly Gln Leu Asp Asn Cys Val Thr Tyr Glu Asn Gly Pro Thr
210                 215                 220

Asn Pro Pro Thr Thr Leu Ile Ala Gly Pro Lys Phe Leu Ala Thr Asn
225                 230                 235                 240

Val Tyr His Leu Ser Pro Ile Glu Asp Leu Ala Leu Ala Thr Ala Leu
                245                 250                 255

Val Arg Pro Leu Tyr Leu Tyr Leu Ala Glu Asp Ile Ser Lys Glu Val
            260                 265                 270

Val Leu Ser Ser Lys Arg Tyr Gly Ser Val Lys Arg Val Phe Ile Val
            275                 280                 285

Ala Thr Glu Asn Asp Ala Leu Lys Lys Glu Phe Leu Lys Leu Met Ile
290                 295                 300

Glu Lys Asn Pro Pro Asp Glu Val Lys Gly Ile Glu Gly Ser Asp His
305                 310                 315                 320

Val Thr Met Met Ser Lys Pro Gln Gln Leu Phe Thr Thr Leu Leu Ser
                325                 330                 335

Ile Ala Asn Lys Tyr Lys
            340

<210> SEQ ID NO 22
<211> LENGTH: 1017
<212> TYPE: DNA
<213> ORGANISM: artificial sequence
<220> FEATURE:
<223> OTHER INFORMATION: Synthetic sequence

<400> SEQUENCE: 22
atggcccaga tcaacaacat ggcccagggc atccagaccc tgaaccctaa ctctaacttc      60
cacaagccgc aagtgcccaa gtctagctcc ttcctcgtgt tcggctccaa gaagctcaag     120
aatagcgcca attccatgct ggtcctgaag aaagactcga tcttcatgca gaagttctgc     180
tcctttcgca tcagtgcttc ggttgcgact gcctgcatgg ctgagaagtc tatgagtcct     240
ttcgttaaga agcacttcgt tctagttcac actgctttcc acggtgcttg gtgctggtac     300
aagattgttg ctttgatgcg tagttctggt cataacgtga ctgctcttga tctcggtgct     360
```

```
agtggtatta acccaaagca agccttgcaa atccccaact ttagcgatta cttgtcacca    420
ctcatggagt ttatggcctc ccttcctgcc aacgagaaga tcatacttgt tggacatgct    480
ttaggagggc tggccatctc aaaagctatg gaaaccttcc ctgagaagat aagcgtggca    540
gtatttctct cgggcctcat gcctggacca aacattgacg caactaccgt ctgtaccaag    600
gctggatctg cagtcttggg gcagttggat aactgcgtga cttatgagaa tgggccgaca    660
aatcctccaa caacccttat tgccggacct aagttcttgg caacgaatgt ctatcatctt    720
tctcccatcg aggatctggc cctcgctact gctcttgtcc gcccacttta cctctatctc    780
gctgaggaca tctcaaaaga agttgtactt catccaaga gatacggctc cgtgaagagg    840
gttttcattg ttgcgacaga gaatgatgca cttaagaaag aatttctgaa gctgatgatc    900
gagaagaatc cacctgacga agtgaaagaa atagaaggct ctgaccatgt gactatgatg    960
tccaaaccac aacagttgtt tacaacgctt ttgagtatcg caaacaagta caagtaa      1017
```

<210> SEQ ID NO 23
<211> LENGTH: 338
<212> TYPE: PRT
<213> ORGANISM: artificial sequence
<220> FEATURE:
<223> OTHER INFORMATION: Synthetic sequence

<400> SEQUENCE: 23

```
Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Ser Phe Leu
            20                  25                  30

Val Phe Gly Ser Lys Lys Leu Lys Asn Ser Ala Asn Ser Met Leu Val
        35                  40                  45

Leu Lys Lys Asp Ser Ile Phe Met Gln Lys Phe Cys Ser Phe Arg Ile
    50                  55                  60

Ser Ala Ser Val Ala Thr Ala Cys Met Ala Glu Lys Ser Met Ser Pro
65                  70                  75                  80

Phe Val Lys Lys His Phe Val Leu Val His Thr Ala Phe His Gly Ala
                85                  90                  95

Trp Cys Trp Tyr Lys Ile Val Ala Leu Met Arg Ser Ser Gly His Asn
            100                 105                 110

Val Thr Ala Leu Asp Leu Gly Ala Ser Gly Ile Asn Pro Lys Gln Ala
        115                 120                 125

Leu Gln Ile Pro Asn Phe Ser Asp Tyr Leu Ser Pro Leu Met Glu Phe
    130                 135                 140

Met Ala Ser Leu Pro Ala Asn Glu Lys Ile Ile Leu Val Gly His Ala
145                 150                 155                 160

Leu Gly Gly Leu Ala Ile Ser Lys Ala Met Glu Thr Phe Pro Glu Lys
                165                 170                 175

Ile Ser Val Ala Val Phe Leu Ser Gly Leu Met Pro Gly Pro Asn Ile
            180                 185                 190

Asp Ala Thr Thr Val Cys Thr Lys Ala Gly Ser Ala Val Leu Gly Gln
        195                 200                 205

Leu Asp Asn Cys Val Thr Tyr Glu Asn Gly Pro Thr Asn Pro Pro Thr
    210                 215                 220

Thr Leu Ile Ala Gly Pro Lys Phe Leu Ala Thr Asn Val Tyr His Leu
225                 230                 235                 240

Ser Pro Ile Glu Asp Leu Ala Leu Ala Thr Ala Leu Val Arg Pro Leu
```

245                 250                 255
Tyr Leu Tyr Leu Ala Glu Asp Ile Ser Lys Glu Val Leu Ser Ser
            260                 265                 270

Lys Arg Tyr Gly Ser Val Lys Arg Val Phe Ile Val Ala Thr Glu Asn
            275                 280                 285

Asp Ala Leu Lys Lys Glu Phe Leu Lys Leu Met Ile Glu Lys Asn Pro
    290                 295                 300

Pro Asp Glu Val Lys Glu Ile Glu Gly Ser Asp His Val Thr Met Met
305                 310                 315                 320

Ser Lys Pro Gln Gln Leu Phe Thr Thr Leu Leu Ser Ile Ala Asn Lys
                325                 330                 335

Tyr Lys

<210> SEQ ID NO 24
<211> LENGTH: 1029
<212> TYPE: DNA
<213> ORGANISM: artificial sequence
<220> FEATURE:
<223> OTHER INFORMATION: Synthetic sequence

<400> SEQUENCE: 24
atggcgcaag ttagcagaat ctgcaatggt gtgcagaacc catctcttat ctccaatctc      60
tcgaaatcca gtcaacgcaa atctccctta tcggtttctc tgaagacgca gcagcatcca     120
cgagcttatc cgatttcgtc gtcgtgggga ttgaagaaga gtgggatgac gttaattggc     180
tctgagcttc gtcctcttaa ggtcatgtct tctgtttcca cggcgtgcat ggctaagaag     240
tctacttcac ctttcgtgaa gaagcacttc gttctagttc acactggttt ccacggtgct     300
tggtgctggt acaagattgt tgctttgatg cgtagttctg gtcacaacgt gactgctctt     360
gatctaggtg ctagtggtat taaccctaag caagcccttg aaatcccaca tttcagcgac     420
tacttgtccc cactcatgga gttcatggct agtttgccgg ccaatgagaa gataattctt     480
gtcggtcatg cactcggagg cttagccatt agcaaggcta tggagacttt cccagagaaa     540
atttcagttg ccgtattcct ctcaggactt atgcccggac taacatcga cgcaaccaca     600
gtttacacta aggcagcgtc tgctgtgatt gggcaattgg acaattacgt tacctacgag     660
aacggcccca ctaacccacc tactacctta atcgccgggc taagtttcct cgctaccaat     720
gtttatcatc tttccccccat cgaggatctt gccctggcaa cggctctggt gagacctgtc     780
tatctctatc ttgctgagga catatccaag gaaatcgtac tgtcctctaa acgttatgga     840
tctgttaaaa gggtctttat tgtggcaacc cagaacgatg cttcaagaa agagtttctc     900
aaattgatga ttgagaaaaa tcctccagac gaagtcaagg agatcgaggg ctcagatcat     960
gtgacaatga tgtcaaaacc acaacagttg tttacaacat tgctgtcgat agcaaataag    1020
tacaagtga                                                            1029

<210> SEQ ID NO 25
<211> LENGTH: 341
<212> TYPE: PRT
<213> ORGANISM: artificial sequence
<220> FEATURE:
<223> OTHER INFORMATION: Synthetic sequence

<400> SEQUENCE: 25

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val

```
            20                  25                  30
Ser Leu Lys Thr Gln Gln His Pro Arg Ala Tyr Pro Ile Ser Ser Ser
         35                  40                  45

Trp Gly Leu Lys Lys Ser Gly Met Thr Leu Ile Gly Ser Glu Leu Arg
 50                  55                  60

Pro Leu Lys Val Met Ser Ser Val Ser Thr Ala Cys Met Ala Lys Lys
 65                  70                  75                  80

Ser Thr Ser Pro Phe Val Lys Lys His Phe Val Leu Val His Thr Gly
                 85                  90                  95

Phe His Gly Ala Trp Cys Trp Tyr Lys Ile Val Ala Leu Met Arg Ser
            100                 105                 110

Ser Gly His Asn Val Thr Ala Leu Asp Leu Gly Ala Ser Gly Ile Asn
        115                 120                 125

Pro Lys Gln Ala Leu Glu Ile Pro His Phe Ser Asp Tyr Leu Ser Pro
    130                 135                 140

Leu Met Glu Phe Met Ala Ser Leu Pro Ala Asn Glu Lys Ile Ile Leu
145                 150                 155                 160

Val Gly His Ala Leu Gly Gly Leu Ala Ile Ser Lys Ala Met Glu Thr
                165                 170                 175

Phe Pro Glu Lys Ile Ser Val Ala Val Phe Leu Ser Gly Leu Met Pro
            180                 185                 190

Gly Pro Asn Ile Asp Ala Thr Thr Val Tyr Thr Lys Ala Ala Ser Ala
        195                 200                 205

Val Ile Gly Gln Leu Asp Asn Tyr Val Thr Tyr Glu Asn Gly Pro Thr
    210                 215                 220

Asn Pro Pro Thr Thr Leu Ile Ala Gly Pro Lys Phe Leu Ala Thr Asn
225                 230                 235                 240

Val Tyr His Leu Ser Pro Ile Glu Asp Leu Ala Leu Ala Thr Ala Leu
                245                 250                 255

Val Arg Pro Val Tyr Leu Tyr Leu Ala Glu Asp Ile Ser Lys Glu Ile
            260                 265                 270

Val Leu Ser Ser Lys Arg Tyr Gly Ser Val Lys Arg Val Phe Ile Val
        275                 280                 285

Ala Thr Gln Asn Asp Ala Phe Lys Lys Glu Phe Leu Lys Leu Met Ile
    290                 295                 300

Glu Lys Asn Pro Pro Asp Glu Val Lys Glu Ile Glu Gly Ser Asp His
305                 310                 315                 320

Val Thr Met Met Ser Lys Pro Gln Gln Leu Phe Thr Thr Leu Leu Ser
                325                 330                 335

Ile Ala Asn Lys Tyr
            340

<210> SEQ ID NO 26
<211> LENGTH: 1017
<212> TYPE: DNA
<213> ORGANISM: artificial sequence
<220> FEATURE:
<223> OTHER INFORMATION: Synthetic sequence

<400> SEQUENCE: 26
atggcccaga tcaacaacat ggcccagggc atccagaccc tgaaccctaa ctctaacttc    60
cacaagccgc aagtgcccaa gtctagctcc ttcctcgtgt tcggctccaa gaagctcaag   120
aatagcgcca attccatgct ggtcctgaag aaagactcga tcttcatgca gaagttctgc   180
tcctttcgca tcagtgcttc ggttgcgact gcctgcatgg ctaagaagtc tacttcacct   240
```

```
ttcgtgaaga agcacttcgt tctagttcac actggtttcc acggtgcttg gtgctggtac    300
aagattgttg ctttgatgcg tagttctggt cacaacgtga ctgctcttga tctaggtgct    360
agtggtatta accctaagca agcccttgaa atcccacatt tcagcgacta cttgtcccca    420
ctcatggagt tcatggctag tttgccggcc aatgagaaga taattcttgt cggtcatgca    480
ctcggaggct tagccattag caaggctatg agactttcc cagagaaaat ttcagttgcc    540
gtattcctct caggacttat gcccggacct aacatcgacg caaccacagt ttacactaag    600
gcagcgtctg ctgtgattgg gcaattggac aattacgtta cctacgagaa cggcccact    660 aacccaccta ctaccttaat cgccgggcct aagtttctcg ctaccaatgt ttatcatctt    720
tcccccatcg aggatcttgc cctggcaacg gctctggtga gacctgtcta tctctatctt    780
gctgaggaca tatccaagga aatcgtactg tcctctaaac gttatggatc tgttaaaagg    840
gtctttattg tggcaaccca gaacgatgct ttcaagaaag agtttctcaa attgatgatt    900
gagaaaaatc ctccagacga agtcaaggag atcgagggct cagatcatgt gacaatgatg    960
tcaaaaccac aacagttgtt tacaacattg ctgtcgatag caaataagta caagtga       1017

<210> SEQ ID NO 27
<211> LENGTH: 338
<212> TYPE: PRT
<213> ORGANISM: artificial sequence
<220> FEATURE:
<223> OTHER INFORMATION: Synthetic sequence

<400> SEQUENCE: 27

Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Ser Phe Leu
            20                  25                  30

Val Phe Gly Ser Lys Lys Leu Lys Asn Ser Ala Asn Ser Met Leu Val
        35                  40                  45

Leu Lys Lys Asp Ser Ile Phe Met Gln Lys Phe Cys Ser Phe Arg Ile
    50                  55                  60

Ser Ala Ser Val Ala Thr Ala Cys Met Ala Lys Lys Ser Thr Ser Pro
65                  70                  75                  80

Phe Val Lys Lys His Phe Val Leu Val His Thr Gly Phe His Gly Ala
                85                  90                  95

Trp Cys Trp Tyr Lys Ile Val Ala Leu Met Arg Ser Ser Gly His Asn
            100                 105                 110

Val Thr Ala Leu Asp Leu Gly Ala Ser Gly Ile Asn Pro Lys Gln Ala
        115                 120                 125

Leu Glu Ile Pro His Phe Ser Asp Tyr Leu Ser Pro Leu Met Glu Phe
    130                 135                 140

Met Ala Ser Leu Pro Ala Asn Glu Lys Ile Ile Leu Val Gly His Ala
145                 150                 155                 160

Leu Gly Gly Leu Ala Ile Ser Lys Ala Met Glu Thr Phe Pro Glu Lys
                165                 170                 175

Ile Ser Val Ala Val Phe Leu Ser Gly Leu Met Pro Gly Pro Asn Ile
            180                 185                 190

Asp Ala Thr Thr Val Tyr Thr Lys Ala Ala Ser Ala Val Ile Gly Gln
        195                 200                 205

Leu Asp Asn Tyr Val Thr Tyr Glu Asn Gly Pro Thr Asn Pro Pro Thr
    210                 215                 220
```

Thr Leu Ile Ala Gly Pro Lys Phe Leu Ala Thr Asn Val Tyr His Leu
225                 230                 235                 240

Ser Pro Ile Glu Asp Leu Ala Leu Ala Thr Ala Leu Val Arg Pro Val
            245                 250                 255

Tyr Leu Tyr Leu Ala Glu Asp Ile Ser Lys Glu Ile Val Leu Ser Ser
        260                 265                 270

Lys Arg Tyr Gly Ser Val Lys Arg Val Phe Ile Val Ala Thr Gln Asn
    275                 280                 285

Asp Ala Phe Lys Lys Glu Phe Leu Lys Leu Met Ile Glu Lys Asn Pro
        290                 295                 300

Pro Asp Glu Val Lys Gly Ile Glu Gly Ser Asp His Val Thr Met Met
305                 310                 315                 320

Ser Lys Pro Gln Gln Leu Phe Thr Thr Leu Leu Ser Ile Ala Asn Lys
                325                 330                 335

Tyr Lys

<210> SEQ ID NO 28
<211> LENGTH: 1026
<212> TYPE: DNA
<213> ORGANISM: artificial sequence
<220> FEATURE:
<223> OTHER INFORMATION: Synthetic sequence

<400> SEQUENCE: 28

```
atggcgcaag ttagcagaat ctgcaatggt gtgcagaacc catctcttat ctccaatctc      60
tcgaaatcca gtcaacgcaa atctccctta tcggtttctc tgaagacgca gcagcatcca     120
cgagcttatc cgatttcgtc gtcgtgggga ttgaagaaga gtgggatgac gttaattggc     180
tctgagcttc gtcctcttaa ggtcatgtct tctgtttcca cggcgtgcat ggaaaagtct     240
atgtcaccct tcgtcaagaa acacttcgtg cttgttcata ctgctttcca cggtgcctgg     300
tgctggtaca gatcgtcgc ccttatgaga agttcaggcc acaacgtgac cgcactggac      360
ctcggggcct ccgggataaa ccccaaacaa gctttgcaga ttcctaactt cagtgattat     420
ctttctccac ttatggagtt tatggcctct cttcccgcta acgaaaagat catactcgtt     480
ggtcattctc ttggtggtct tgccatttct aaagcaatgg aaaccttccc tgagaaaata     540
tcagtggctg ttttcttgtc cggtcttatg cccggaccta atattgacgc aacaaccgtt     600
tgtaccaagg ctgggtccgc cgtgttgggc caactcgaca actgcgtgac ctacgaaaat     660
ggtcctacta atccacctac tacccttatc gcaggaccta gtttctcgc tacaaacgtg     720
taccacctct ctccaataga ggatctggct cttgccactg ctttggtcag gcctctttat     780
ctgtacctcg ctgaggacat atctaaagaa gttgtgcttt cttctaagcg ttatggttcc     840
gtgaagcgtg tcttcatagt ggcaacagag aatgatgctc ttaagaaaga gtttctcaaa     900
ctgatgatcg agaagaatcc acctgatgaa gtgaaagaaa ttgagggttc tgaccatgtt     960
accatgatgt caaagcctca acagttgttt accacattgc ttagtatagc taataagtat    1020
aaataa                                                                1026
```

<210> SEQ ID NO 29
<211> LENGTH: 341
<212> TYPE: PRT
<213> ORGANISM: artificial sequence
<220> FEATURE:
<223> OTHER INFORMATION: Synthetic sequence

<400> SEQUENCE: 29

```
Met Ala Gln Val Ser Arg Ile Cys Asn Gly Val Gln Asn Pro Ser Leu
1               5                  10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
            35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys Met Glu Lys Ser
65                  70                  75                  80

Met Ser Pro Phe Val Lys Lys His Phe Val Leu Val His Thr Ala Phe
                85                  90                  95

His Gly Ala Trp Cys Trp Tyr Lys Ile Val Ala Leu Met Arg Ser Ser
                100                 105                 110

Gly His Asn Val Thr Ala Leu Asp Leu Gly Ala Ser Gly Ile Asn Pro
            115                 120                 125

Lys Gln Ala Leu Gln Ile Pro Asn Phe Ser Asp Tyr Leu Ser Pro Leu
        130                 135                 140

Met Glu Phe Met Ala Ser Leu Pro Ala Asn Glu Lys Ile Ile Leu Val
145                 150                 155                 160

Gly His Ser Leu Gly Gly Leu Ala Ile Ser Lys Ala Met Glu Thr Phe
                165                 170                 175

Pro Glu Lys Ile Ser Val Ala Val Phe Leu Ser Gly Leu Met Pro Gly
            180                 185                 190

Pro Asn Ile Asp Ala Thr Thr Val Cys Thr Lys Ala Gly Ser Ala Val
            195                 200                 205

Leu Gly Gln Leu Asp Asn Cys Val Thr Tyr Glu Asn Gly Pro Thr Asn
    210                 215                 220

Pro Pro Thr Thr Leu Ile Ala Gly Pro Lys Phe Leu Ala Thr Asn Val
225                 230                 235                 240

Tyr His Leu Ser Pro Ile Glu Asp Leu Ala Leu Ala Thr Ala Leu Val
                245                 250                 255

Arg Pro Leu Tyr Leu Tyr Leu Ala Glu Asp Ile Ser Lys Glu Val Val
            260                 265                 270

Leu Ser Ser Lys Arg Tyr Gly Ser Val Lys Arg Val Phe Ile Val Ala
    275                 280                 285

Thr Glu Asn Asp Ala Leu Lys Lys Glu Phe Leu Lys Leu Met Ile Glu
290                 295                 300

Lys Asn Pro Pro Asp Glu Val Lys Glu Ile Glu Gly Ser Asp His Val
305                 310                 315                 320

Thr Met Met Ser Lys Pro Gln Gln Leu Phe Thr Thr Leu Leu Ser Ile
                325                 330                 335

Ala Asn Lys Tyr Lys
            340

<210> SEQ ID NO 30
<211> LENGTH: 1026
<212> TYPE: DNA
<213> ORGANISM: artificial sequence
<220> FEATURE:
<223> OTHER INFORMATION: Synthetic sequence

<400> SEQUENCE: 30
atggcgcaag ttagcagaat ctgcaatggt gtgcagaacc catctcttat ctccaatctc      60
tcgaaatcca gtcaacgcaa atctccctta tcggtttctc tgaagacgca gcagcatcca     120
```

```
cgagcttatc cgatttcgtc gtcgtgggga ttgaagaaga gtgggatgac gttaattggc      180
tctgagcttc gtcctcttaa ggtcatgtct tctgtttcca cggcgtgcat ggaaaagtct      240
atgtcaccct tcgtcaagaa acacttcgtg cttgttcata ctgctttcca cggtgcctgg      300
tgctggtaca agatcgtcgc ccttatgaga agttcaggcc acaacgtgac cgcactggac      360
ctcggggcct ccgggataaa ccccaaacaa gctttgcaga ttcctaactt cagtgattat      420
ctttctccac ttatggagtt tatggcctct cttcccgcta acgaaaagat catactcgtt      480
ggtcatgctc ttggtggtct tgccatttct aaagcaatgg aaaccttccc tgagaaaata      540
tcagtggctg ttttcttgtc cggtcttatg cccggaccta atattgacgc aacaaccgtt      600
tgtaccaagg ctgggtccgc cgtgttgggc caactcgaca actgcgtgac ctacgaaaat      660
ggtcctacta atccacctac tacccttatc gcaggaccta agtttctcgc tacaaacgtg      720
taccacctct ctccaataga ggatctggct cttgccactg ctttggtcag gcctctttat      780
ctgtacctcg ctgaggacat atctaaagaa gttgtgcttt cttctaagcg ttatggttcc      840
gtgaagcgtg tcttcatagt ggcaacagag gatgatgctc ttaagaaaga gtttctcaaa      900
ctgatgatcg agaagaatcc acctgatgaa gtgaaagaaa ttgagggttc tgaccatgtt      960
accatgatgt caaagcctca acagttgttt accacattgc ttagtatagc taataagtat     1020
aaataa                                                                1026
```

<210> SEQ ID NO 31
<211> LENGTH: 341
<212> TYPE: PRT
<213> ORGANISM: artificial sequence
<220> FEATURE:
<223> OTHER INFORMATION: Synthetic sequence

<400> SEQUENCE: 31

```
Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys Met Glu Lys Ser
65                  70                  75                  80

Met Ser Pro Phe Val Lys Lys His Phe Val Leu Val His Thr Ala Phe
                85                  90                  95

His Gly Ala Trp Cys Trp Tyr Lys Val Ala Leu Met Arg Ser Ser
            100                 105                 110

Gly His Asn Val Thr Ala Leu Asp Leu Gly Ala Ser Gly Ile Asn Pro
        115                 120                 125

Lys Gln Ala Leu Gln Ile Pro Asn Phe Ser Asp Tyr Leu Ser Pro Leu
    130                 135                 140

Met Glu Phe Met Ala Ser Leu Pro Ala Asn Glu Lys Ile Ile Leu Val
145                 150                 155                 160

Gly His Ala Leu Gly Gly Leu Ala Ile Ser Lys Ala Met Glu Thr Phe
                165                 170                 175

Pro Glu Lys Ile Ser Val Ala Val Phe Leu Ser Gly Leu Met Pro Gly
            180                 185                 190
```

Pro Asn Ile Asp Ala Thr Thr Val Cys Thr Lys Ala Gly Ser Ala Val
            195                 200                 205
Leu Gly Gln Leu Asp Asn Cys Val Thr Tyr Glu Asn Gly Pro Thr Asn
        210                 215                 220
Pro Pro Thr Thr Leu Ile Ala Gly Pro Lys Phe Leu Ala Thr Asn Val
225                 230                 235                 240
Tyr His Leu Ser Pro Ile Glu Asp Leu Ala Leu Ala Thr Ala Leu Val
                245                 250                 255
Arg Pro Leu Tyr Leu Tyr Leu Ala Glu Asp Ile Ser Lys Glu Val Val
            260                 265                 270
Leu Ser Ser Lys Arg Tyr Gly Ser Val Lys Arg Val Phe Ile Val Ala
        275                 280                 285
Thr Glu Asp Asp Ala Leu Lys Lys Glu Phe Leu Lys Leu Met Ile Glu
290                 295                 300
Lys Asn Pro Pro Asp Glu Val Lys Glu Ile Glu Gly Ser Asp His Val
305                 310                 315                 320
Thr Met Met Ser Lys Pro Gln Gln Leu Phe Thr Thr Leu Leu Ser Ile
                325                 330                 335
Ala Asn Lys Tyr Lys
            340

<210> SEQ ID NO 32
<211> LENGTH: 1026
<212> TYPE: DNA
<213> ORGANISM: artificial sequence
<220> FEATURE:
<223> OTHER INFORMATION: Synthetic sequence

<400> SEQUENCE: 32
atggcgcaag ttagcagaat ctgcaatggt gtgcagaacc catctcttat ctccaatctc      60
tcgaaatcca gtcaacgcaa atctccctta tcggtttctc tgaagacgca gcagcatcca     120
cgagcttatc cgatttcgtc gtcgtgggga ttgaagaaga gtgggatgac gttaattggc     180
tctgagcttc gtcctcttaa ggtcatgtct tctgtttcca cggcgtgcat ggaaaagtct     240
atgtcaccct tcgtcaagaa acacttcgtg cttgttcata ctgctttcca cggtgcctgg     300
tgctggtaca agatcgtcgc ccttatgaga agttcaggcc acaacgtgac cgcactggac     360
ctcggggcct ccgggataaa ccccaaacaa gctttgcaga ttcctaactt cagtgattat     420
ctttctccac ttatggagtt tatggcctct cttcccgcta acgaaaagat catactcgtt     480
ggtcattctc ttggtggtct tgccatttct aaagcaatgg aaaccttccc tgagaaaata     540
tcagtggctg ttttcttgtc cggtcttatg cccggaccta atattgacgc aacaaccgtt     600
tgtaccaagg ctgggtccgc cgtgttgggc aactcgaca actgcgtgac ctacgaaaat     660
ggtcctacta atccacctac taccttatc gcaggaccta gtttctcgc tacaaacgtg     720
taccacctct ctccaataga ggatctggct cttgccactg ctttggtcag gcctctttat     780
ctgtacctcg ctgaggacat atctaaagaa gttgtgcttt cttctaagcg ttatggttcc     840
gtgaagcgtg tcttcatagt ggcaacagag gatgatgctc ttaagaaaga gtttctcaaa     900
ctgatgatcg agaagaatcc acctgatgaa gtgaaagaaa ttgagggttc tgaccatgtt     960
accatgatgt caaagcctca acagttgttt accacattgc ttagtatagc taataagtat    1020
aaataa                                                                1026

<210> SEQ ID NO 33
<211> LENGTH: 341

```
<212> TYPE: PRT
<213> ORGANISM: artificial sequence
<220> FEATURE:
<223> OTHER INFORMATION: Synthetic sequence

<400> SEQUENCE: 33
```

| | | | | | | | | | | | | | | |
|---|---|---|---|---|---|---|---|---|---|---|---|---|---|---|
| Met | Ala | Gln | Val | Ser | Arg | Ile | Cys | Asn | Gly | Val | Gln | Asn | Pro | Ser | Leu |
| 1 | | | | 5 | | | | | 10 | | | | | 15 | |
| Ile | Ser | Asn | Leu | Ser | Lys | Ser | Ser | Gln | Arg | Lys | Ser | Pro | Leu | Ser | Val |
| | | | | 20 | | | | | 25 | | | | | 30 | |
| Ser | Leu | Lys | Thr | Gln | Gln | His | Pro | Arg | Ala | Tyr | Pro | Ile | Ser | Ser | Ser |
| | | | | 35 | | | | | 40 | | | | | 45 | |
| Trp | Gly | Leu | Lys | Lys | Ser | Gly | Met | Thr | Leu | Ile | Gly | Ser | Glu | Leu | Arg |
| 50 | | | | | 55 | | | | | 60 | | | | | |
| Pro | Leu | Lys | Val | Met | Ser | Ser | Val | Ser | Thr | Ala | Cys | Met | Glu | Lys | Ser |
| 65 | | | | | 70 | | | | | 75 | | | | | 80 |
| Met | Ser | Pro | Phe | Val | Lys | Lys | His | Phe | Val | Leu | Val | His | Thr | Ala | Phe |
| | | | | 85 | | | | | 90 | | | | | 95 | |
| His | Gly | Ala | Trp | Cys | Trp | Tyr | Lys | Ile | Val | Ala | Leu | Met | Arg | Ser | Ser |
| | | | | 100 | | | | | 105 | | | | | 110 | |
| Gly | His | Asn | Val | Thr | Ala | Leu | Asp | Leu | Gly | Ala | Ser | Gly | Ile | Asn | Pro |
| | | | | 115 | | | | | 120 | | | | | 125 | |
| Lys | Gln | Ala | Leu | Gln | Ile | Pro | Asn | Phe | Ser | Asp | Tyr | Leu | Ser | Pro | Leu |
| 130 | | | | | 135 | | | | | 140 | | | | | |
| Met | Glu | Phe | Met | Ala | Ser | Leu | Pro | Ala | Asn | Glu | Lys | Ile | Ile | Leu | Val |
| 145 | | | | | 150 | | | | | 155 | | | | | 160 |
| Gly | His | Ser | Leu | Gly | Gly | Leu | Ala | Ile | Ser | Lys | Ala | Met | Glu | Thr | Phe |
| | | | | 165 | | | | | 170 | | | | | 175 | |
| Pro | Glu | Lys | Ile | Ser | Val | Ala | Val | Phe | Leu | Ser | Gly | Leu | Met | Pro | Gly |
| | | | | 180 | | | | | 185 | | | | | 190 | |
| Pro | Asn | Ile | Asp | Ala | Thr | Thr | Val | Cys | Thr | Lys | Ala | Gly | Ser | Ala | Val |
| | | | | 195 | | | | | 200 | | | | | 205 | |
| Leu | Gly | Gln | Leu | Asp | Asn | Cys | Val | Thr | Tyr | Glu | Asn | Gly | Pro | Thr | Asn |
| 210 | | | | | 215 | | | | | 220 | | | | | |
| Pro | Pro | Thr | Thr | Leu | Ile | Ala | Gly | Pro | Lys | Phe | Leu | Ala | Thr | Asn | Val |
| 225 | | | | | 230 | | | | | 235 | | | | | 240 |
| Tyr | His | Leu | Ser | Pro | Ile | Glu | Asp | Leu | Ala | Leu | Ala | Thr | Ala | Leu | Val |
| | | | | 245 | | | | | 250 | | | | | 255 | |
| Arg | Pro | Leu | Tyr | Leu | Tyr | Leu | Ala | Glu | Asp | Ile | Ser | Lys | Glu | Val | Val |
| | | | | 260 | | | | | 265 | | | | | 270 | |
| Leu | Ser | Ser | Lys | Arg | Tyr | Gly | Ser | Val | Lys | Arg | Val | Phe | Ile | Val | Ala |
| | | | | 275 | | | | | 280 | | | | | 285 | |
| Thr | Glu | Asp | Asp | Ala | Leu | Lys | Lys | Glu | Phe | Leu | Lys | Leu | Met | Ile | Glu |
| 290 | | | | | 295 | | | | | 300 | | | | | |
| Lys | Asn | Pro | Pro | Asp | Glu | Val | Lys | Glu | Ile | Glu | Gly | Ser | Asp | His | Val |
| 305 | | | | | 310 | | | | | 315 | | | | | 320 |
| Thr | Met | Met | Ser | Lys | Pro | Gln | Gln | Leu | Phe | Thr | Thr | Leu | Leu | Ser | Ile |
| | | | | 325 | | | | | 330 | | | | | 335 | |
| Ala | Asn | Lys | Tyr | Lys | | | | | | | | | | | |
| | | | | 340 | | | | | | | | | | | |

```
<210> SEQ ID NO 34
<211> LENGTH: 1029
<212> TYPE: DNA
<213> ORGANISM: artificial sequence
<220> FEATURE:
```

-continued

<223> OTHER INFORMATION: Synthetic sequence

<400> SEQUENCE: 34

```
atggcgcaag ttagcagaat ctgcaatggt gtgcagaacc catctcttat ctccaatctc    60
tcgaaatcca gtcaacgcaa atctccctta tcggtttctc tgaagacgca gcagcatcca   120
cgagcttatc cgatttcgtc gtcgtgggga ttgaagaaga gtgggatgac gttaattggc   180
tctgagcttc gtcctcttaa ggtcatgtct tctgtttcca cggcgtgcat ggctaagaag   240
tctacttcac ctttcgtgaa gaagcacttc gttctagttc acactggttt ccacggtgct   300
tggtgctggt acaagattgt tgctttgatg cgtagttctg gtcacaacgt gactgctctt   360
gatctaggtg ctagtggtat taaccctaag caagcccttg aaatcccaca tttcagcgac   420
tacttgtccc cactcatgga gttcatggct agtttgccgg ccaatgagaa gataattctt   480
gtcggtcatt cactcggagg cttagccatt agcaaggcta tggagacttt cccagagaaa   540
atttcagttg ccgtattcct ctcaggactt atgcccggac ctaacatcga cgcaaccaca   600
gtttacacta aggcagcgtc tgctgtgatt gggcaattgg acaattacgt tacctacgag   660
aacggcccca ctaacccacc tactacctta atcgccgggc taagtttcct cgctaccaat   720
gtttatcatc tttccccccat cgaggatctt gccctggcaa cggctctggt gagacctgtc   780
tatctctatc ttgctgagga catatccaag gaaatcgtac tgtcctctaa acgttatgga   840
tctgttaaaa gggtctttat tgtggcaacc cagaacgatg cttttcaagaa agagtttctc   900
aaattgatga ttgagaaaaa tcctccagac gaagtcaagg agatcgaggg ctcagatcat   960
gtgacaatga tgtcaaaacc acaacagttg tttacaacat tgctgtcgat agcaaataag  1020
tacaagtga                                                          1029
```

<210> SEQ ID NO 35
<211> LENGTH: 342
<212> TYPE: PRT
<213> ORGANISM: artificial sequence
<220> FEATURE:
<223> OTHER INFORMATION: Synthetic sequence

<400> SEQUENCE: 35

```
Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys Met Ala Lys Lys
65                  70                  75                  80

Ser Thr Ser Pro Phe Val Lys Lys His Phe Val Leu Val His Thr Gly
                85                  90                  95

Phe His Gly Ala Trp Cys Trp Tyr Lys Ile Val Ala Leu Met Arg Ser
            100                 105                 110

Ser Gly His Asn Val Thr Ala Leu Asp Leu Gly Ala Ser Gly Ile Asn
        115                 120                 125

Pro Lys Gln Ala Leu Glu Ile Pro His Phe Ser Asp Tyr Leu Ser Pro
    130                 135                 140

Leu Met Glu Phe Met Ala Ser Leu Pro Ala Asn Glu Lys Ile Ile Leu
145                 150                 155                 160
```

```
Val Gly His Ser Leu Gly Gly Leu Ala Ile Ser Lys Ala Met Glu Thr
            165                 170                 175
Phe Pro Glu Lys Ile Ser Val Ala Val Phe Leu Ser Gly Leu Met Pro
        180                 185                 190
Gly Pro Asn Ile Asp Ala Thr Thr Val Tyr Thr Lys Ala Ala Ser Ala
    195                 200                 205
Val Ile Gly Gln Leu Asp Asn Tyr Val Thr Tyr Glu Asn Gly Pro Thr
210                 215                 220
Asn Pro Pro Thr Thr Leu Ile Ala Gly Pro Lys Phe Leu Ala Thr Asn
225                 230                 235                 240
Val Tyr His Leu Ser Pro Ile Glu Asp Leu Ala Leu Ala Thr Ala Leu
                245                 250                 255
Val Arg Pro Val Tyr Leu Tyr Leu Ala Glu Asp Ile Ser Lys Glu Ile
            260                 265                 270
Val Leu Ser Ser Lys Arg Tyr Gly Ser Val Lys Arg Val Phe Ile Val
        275                 280                 285
Ala Thr Gln Asn Asp Ala Phe Lys Lys Glu Phe Leu Lys Leu Met Ile
    290                 295                 300
Glu Lys Asn Pro Pro Asp Glu Val Lys Glu Ile Glu Gly Ser Asp His
305                 310                 315                 320
Val Thr Met Met Ser Lys Pro Gln Gln Leu Phe Thr Thr Leu Leu Ser
                325                 330                 335
Ile Ala Asn Lys Tyr Lys
                340

<210> SEQ ID NO 36
<211> LENGTH: 1029
<212> TYPE: DNA
<213> ORGANISM: artificial sequence
<220> FEATURE:
<223> OTHER INFORMATION: Synthetic sequence

<400> SEQUENCE: 36
atggcgcaag ttagcagaat ctgcaatggt gtgcagaacc catctcttat ctccaatctc    60
tcgaaatcca gtcaacgcaa atctccctta tcggtttctc tgaagacgca gcagcatcca   120
cgagcttatc cgatttcgtc gtcgtgggga ttgaagaaga gtgggatgac gttaattggc   180
tctgagcttc gtcctcttaa ggtcatgtct ctgtttcca cggcgtgcat ggctaagaag    240
tctacttcac ctttcgtgaa gaagcacttc gttctagttc acactggttt ccacggtgct   300
tggtgctggt acaagattgt tgctttgatg cgtagttctg gtcacaacgt gactgctctt   360
gatctaggtg ctagtggtat taaccctaag caagcccttg aaatcccaca tttcagcgac   420
tacttgtccc cactcatgga gttcatggct agtttgccgg ccaatgagaa gataattctt   480
gtcggtcatg cactcggagg cttagccatt agcaaggcta tggagacttt cccagagaaa   540
atttcagttg ccgtattcct ctcaggactt atgcccggac taacatcga cgcaaccaca   600 gtttacacta aggcagcgtc tgctgtgatt gggcaattgg acaattacgt tacctacgag   660
aacggcccca ctaacccacc tactacctta atcgccgggc taagtttct cgctaccaat    720 gtttatcatc tttccccccat cgaggatctt gccctggcaa cggctctggt gagacctgtc   780
tatctctatc ttgctgagga catatccaag gaaatcgtac tgtcctctaa acgttatgga   840
tctgttaaaa gggtctttat tgtggcaacc caggacgatg ctttcaagaa agagtttctc   900
aaattgatga ttgagaaaaa tcctccagac gaagtcaagg agatcgaggg ctcagatcat   960
```

```
gtgacaatga tgtcaaaacc acaacagttg tttacaacat tgctgtcgat agcaaataag    1020
tacaagtga                                                             1029
```

<210> SEQ ID NO 37
<211> LENGTH: 342
<212> TYPE: PRT
<213> ORGANISM: artificial sequence
<220> FEATURE:
<223> OTHER INFORMATION: Synthetic sequence

<400> SEQUENCE: 37

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys Met Ala Lys Lys
65                  70                  75                  80

Ser Thr Ser Pro Phe Val Lys Lys His Phe Val Leu Val His Thr Gly
                85                  90                  95

Phe His Gly Ala Trp Cys Trp Tyr Lys Ile Val Ala Leu Met Arg Ser
            100                 105                 110

Ser Gly His Asn Val Thr Ala Leu Asp Leu Gly Ala Ser Gly Ile Asn
        115                 120                 125

Pro Lys Gln Ala Leu Glu Ile Pro His Phe Ser Asp Tyr Leu Ser Pro
    130                 135                 140

Leu Met Glu Phe Met Ala Ser Leu Pro Ala Asn Glu Lys Ile Ile Leu
145                 150                 155                 160

Val Gly His Ala Leu Gly Gly Leu Ala Ile Ser Lys Ala Met Glu Thr
                165                 170                 175

Phe Pro Glu Lys Ile Ser Val Ala Val Phe Leu Ser Gly Leu Met Pro
            180                 185                 190

Gly Pro Asn Ile Asp Ala Thr Thr Val Tyr Thr Lys Ala Ala Ser Ala
        195                 200                 205

Val Ile Gly Gln Leu Asp Asn Tyr Val Thr Tyr Glu Asn Gly Pro Thr
    210                 215                 220

Asn Pro Pro Thr Thr Leu Ile Ala Gly Pro Lys Phe Leu Ala Thr Asn
225                 230                 235                 240

Val Tyr His Leu Ser Pro Ile Glu Asp Leu Ala Leu Ala Thr Ala Leu
                245                 250                 255

Val Arg Pro Val Tyr Leu Tyr Leu Ala Glu Asp Ile Ser Lys Glu Ile
            260                 265                 270

Val Leu Ser Ser Lys Arg Tyr Gly Ser Val Lys Arg Val Phe Ile Val
        275                 280                 285

Ala Thr Gln Asp Asp Ala Phe Lys Lys Glu Phe Leu Lys Leu Met Ile
    290                 295                 300

Glu Lys Asn Pro Pro Asp Glu Val Lys Glu Ile Glu Gly Ser Asp His
305                 310                 315                 320

Val Thr Met Met Ser Lys Pro Gln Gln Leu Phe Thr Thr Leu Leu Ser
                325                 330                 335

Ile Ala Asn Lys Tyr Lys
            340

```
<210> SEQ ID NO 38
<211> LENGTH: 1029
<212> TYPE: DNA
<213> ORGANISM: artificial sequence
<220> FEATURE:
<223> OTHER INFORMATION: Synthetic sequence

<400> SEQUENCE: 38
atggcgcaag ttagcagaat ctgcaatggt gtgcagaacc catctcttat ctccaatctc    60
tcgaaatcca gtcaacgcaa atctccctta tcggtttctc tgaagacgca gcagcatcca   120
cgagcttatc cgatttcgtc gtcgtgggga ttgaagaaga gtgggatgac gttaattggc   180
tctgagcttc gtcctcttaa ggtcatgtct ctgtttcca cggcgtgcat ggctaagaag    240
tctacttcac ctttcgtgaa gaagcacttc gttctagttc acactggttt ccacggtgct   300
tggtgctggt acaagattgt tgctttgatg cgtagttctg gtcacaacgt gactgctctt   360
gatctaggtg ctagtggtat taaccctaag caagcccttg aaatcccaca tttcagcgac   420
tacttgtccc cactcatgga gttcatggct agtttgccgg ccaatgagaa gataattctt   480
gtcggtcatt cactcggagg cttagccatt agcaaggcta tggagacttt cccagagaaa   540
atttcagttg ccgtattcct ctcaggactt atgcccggac taacatcga cgcaaccaca    600 gtttacacta aggcagcgtc tgctgtgatt gggcaattgg acaattacgt tacctacgag   660
aacggcccca ctaacccacc tactacctta atcgccgggc taagtttct cgctaccaat    720 gtttatcatc tttcccccat cgaggatctt gccctggcaa cggctctggt gagacctgtc   780
tatctctatc ttgctgagga catatccaag gaaatcgtac tgtcctctaa acgttatgga   840
tctgttaaaa gggtctttat tgtggcaacc caggacgatg ctttcaagaa agagtttctc   900
aaattgatga ttgagaaaaa tcctccagac gaagtcaagg agatcgaggg ctcagatcat   960
gtgacaatga tgtcaaaacc acaacagttg tttacaacat tgctgtcgat agcaaataag  1020
tacaagtga                                                           1029

<210> SEQ ID NO 39
<211> LENGTH: 342
<212> TYPE: PRT
<213> ORGANISM: artificial sequence
<220> FEATURE:
<223> OTHER INFORMATION: Synthetic sequence

<400> SEQUENCE: 39
```

Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Cys Met Ala Lys Lys
65                  70                  75                  80

Ser Thr Ser Pro Phe Val Lys Lys His Phe Val Leu Val His Thr Gly
                85                  90                  95

Phe His Gly Ala Trp Cys Trp Tyr Lys Ile Val Ala Leu Met Arg Ser
            100                 105                 110

Ser Gly His Asn Val Thr Ala Leu Asp Leu Gly Ala Ser Gly Ile Asn

```
                 115                 120                 125
Pro Lys Gln Ala Leu Glu Ile Pro His Phe Ser Asp Tyr Leu Ser Pro
        130                 135                 140

Leu Met Glu Phe Met Ala Ser Leu Pro Ala Asn Glu Lys Ile Ile Leu
145                 150                 155                 160

Val Gly His Ser Leu Gly Gly Leu Ala Ile Ser Lys Ala Met Glu Thr
                165                 170                 175

Phe Pro Glu Lys Ile Ser Val Ala Val Phe Leu Ser Gly Leu Met Pro
            180                 185                 190

Gly Pro Asn Ile Asp Ala Thr Thr Val Tyr Thr Lys Ala Ala Ser Ala
        195                 200                 205

Val Ile Gly Gln Leu Asp Asn Tyr Val Thr Tyr Glu Asn Gly Pro Thr
    210                 215                 220

Asn Pro Pro Thr Thr Leu Ile Ala Gly Pro Lys Phe Leu Ala Thr Asn
225                 230                 235                 240

Val Tyr His Leu Ser Pro Ile Glu Asp Leu Ala Leu Ala Thr Ala Leu
                245                 250                 255

Val Arg Pro Val Tyr Leu Tyr Leu Ala Glu Asp Ile Ser Lys Glu Ile
            260                 265                 270

Val Leu Ser Ser Lys Arg Tyr Gly Ser Val Lys Arg Val Phe Ile Val
        275                 280                 285

Ala Thr Gln Asp Asp Ala Phe Lys Lys Glu Phe Leu Lys Leu Met Ile
    290                 295                 300

Glu Lys Asn Pro Pro Asp Glu Val Lys Glu Ile Glu Gly Ser Asp His
305                 310                 315                 320

Val Thr Met Met Ser Lys Pro Gln Gln Leu Phe Thr Thr Leu Leu Ser
                325                 330                 335

Ile Ala Asn Lys Tyr Lys
            340

<210> SEQ ID NO 40
<211> LENGTH: 411
<212> TYPE: DNA
<213> ORGANISM: Lycopersicon hirsutum

<400> SEQUENCE: 40
atggcttctg ttactggatc ttccttcgcc atctcttccc tttcctcctc cttcaacccc      60
aacaaggcat gtttgaagac atcctccctt tctatcaagg gaataagctt cccttccctc     120
agagtgaagc cagctactcg tcgcttcagc attagctgtg cggctaaacc agagacagtt     180
gacaaagtgt gtgaaattgt gaagaaacaa ctggctcttc ccaatgattc tgcagtcaat     240
ggagagtcca aatttatagc acttggtgct gattctcttg acacggttga gattgtcatg     300
ggacttgagg aagcatttgg aatcactgtt gaagaagaga atgcacagac tattgcaaca     360
gttcaagatg ctgctgactt gattgaggat ctcgttgcca gaaatgttaa                411

<210> SEQ ID NO 41
<211> LENGTH: 136
<212> TYPE: PRT
<213> ORGANISM: Lycopersicon hirsutum

<400> SEQUENCE: 41

Met Ala Ser Val Thr Gly Ser Ser Phe Ala Ile Ser Ser Leu Ser Ser
1               5                   10                  15

Ser Phe Asn Pro Asn Lys Ala Cys Leu Lys Thr Ser Ser Leu Ser Ile
            20                  25                  30
```

Lys Gly Ile Ser Phe Pro Ser Leu Arg Val Lys Pro Ala Thr Arg Arg
         35                  40                  45

Phe Ser Ile Ser Cys Ala Ala Lys Pro Glu Thr Val Asp Lys Val Cys
 50                  55                  60

Glu Ile Val Lys Lys Gln Leu Ala Leu Pro Asn Asp Ser Ala Val Asn
65                  70                  75                  80

Gly Glu Ser Lys Phe Ile Ala Leu Gly Ala Asp Ser Leu Asp Thr Val
                 85                  90                  95

Glu Ile Val Met Gly Leu Glu Glu Ala Phe Gly Ile Thr Val Glu Glu
             100                 105                 110

Glu Asn Ala Gln Thr Ile Ala Thr Val Gln Asp Ala Ala Asp Leu Ile
         115                 120                 125

Glu Asp Leu Val Ala Lys Lys Cys
         130                 135

<210> SEQ ID NO 42
<211> LENGTH: 411
<212> TYPE: DNA
<213> ORGANISM: Lycopersicon hirsutum

<400> SEQUENCE: 42
atggcttctg ttacaggctc atcagctacc gccatgtcct gctccttcaa ggcacctaac     60
cgtgtatcga atttgaagac atcttctctt tcattcaagg ggattagcta ctcttccatc    120
agagtgaatc cagccactcg tcgcctcagt attacttgtg cggctaagcc agagactgtc    180
aacaaagtgt gtgacattgt gaagaaacaa ctagctcttt ctgctgatac tgatgtctgt    240
ggagattcaa agtttgctgc gcttggtgct gattctcttg atacggtgga gattgtcatg    300
ggacttgagg aagagtttgg catctcggtg gaagaagaca gtgctcagag tattgcaaca    360
gttcaagatg ctgcagacct gattgaggat ctcatttcaa agaaagcttg a              411

<210> SEQ ID NO 43
<211> LENGTH: 136
<212> TYPE: PRT
<213> ORGANISM: Lycopersicon hirsutum

<400> SEQUENCE: 43

Met Ala Ser Val Thr Gly Ser Ser Ala Thr Ala Met Ser Cys Ser Phe
1                5                  10                  15

Lys Ala Pro Asn Arg Val Ser Asn Leu Lys Thr Ser Ser Leu Ser Phe
             20                  25                  30

Lys Gly Ile Ser Tyr Ser Ser Ile Arg Val Asn Pro Ala Thr Arg Arg
         35                  40                  45

Leu Ser Ile Thr Cys Ala Ala Lys Pro Glu Thr Val Asn Lys Val Cys
 50                  55                  60

Asp Ile Val Lys Lys Gln Leu Ala Leu Ser Ala Asp Thr Asp Val Cys
65                  70                  75                  80

Gly Asp Ser Lys Phe Ala Ala Leu Gly Ala Asp Ser Leu Asp Thr Val
                 85                  90                  95

Glu Ile Val Met Gly Leu Glu Glu Glu Phe Gly Ile Ser Val Glu Glu
             100                 105                 110

Asp Ser Ala Gln Ser Ile Ala Thr Val Gln Asp Ala Ala Asp Leu Ile
         115                 120                 125

Glu Asp Leu Ile Ser Lys Lys Ala
         130                 135

<210> SEQ ID NO 44
<211> LENGTH: 411
<212> TYPE: DNA
<213> ORGANISM: Lycopersicon hirsutum

<400> SEQUENCE: 44

| | | | | | |
|---|---|---|---|---|---|
| atggcttctg | ttactggatc | ttccttcgcc | atctcctccc | tttcctcctc | cttcaacccc | 60 |
| aacaaggcat | gtttgaagac | atcctcccct | tctatcaagg | gaataagctt | cccttccctc | 120 |
| agagtgaagc | cagctactcg | tcacttcagc | attagctgtg | cggctaaacc | agagacagtt | 180 |
| gacaaagtgt | gtgaaattgt | gaagaaacaa | ctggctcttc | ccaatgattc | tgcagtcaat | 240 |
| ggagagtcca | aatttatagc | acttggtgct | gattctcttg | acacggttga | gattgtcatg | 300 |
| ggacttgagg | aagcatttgg | aatcactgtt | gaagaagaga | acgcacagac | tattgcaaca | 360 |
| gttcaagatg | ctgctgactt | gattgaggat | cttgtcgcca | agaaatgtta | a | 411 |

<210> SEQ ID NO 45
<211> LENGTH: 136
<212> TYPE: PRT
<213> ORGANISM: Lycopersicon hirsutum

<400> SEQUENCE: 45

Met Ala Ser Val Thr Gly Ser Ser Phe Ala Ile Ser Ser Leu Ser Ser
1               5                   10                  15

Ser Phe Asn Pro Asn Lys Ala Cys Leu Lys Thr Ser Ser Leu Ser Ile
            20                  25                  30

Lys Gly Ile Ser Phe Pro Ser Leu Arg Val Lys Pro Ala Thr Arg His
        35                  40                  45

Phe Ser Ile Ser Cys Ala Ala Lys Pro Glu Thr Val Asp Lys Val Cys
    50                  55                  60

Glu Ile Val Lys Lys Gln Leu Ala Leu Pro Asn Asp Ser Ala Val Asn
65                  70                  75                  80

Gly Glu Ser Lys Phe Ile Ala Leu Gly Ala Asp Ser Leu Asp Thr Val
                85                  90                  95

Glu Ile Val Met Gly Leu Glu Glu Ala Phe Gly Ile Thr Val Glu Glu
            100                 105                 110

Glu Asn Ala Gln Thr Ile Ala Thr Val Gln Asp Ala Ala Asp Leu Ile
        115                 120                 125

Glu Asp Leu Val Ala Lys Lys Cys
    130                 135

<210> SEQ ID NO 46
<211> LENGTH: 411
<212> TYPE: DNA
<213> ORGANISM: Lycopersicon esculentum

<400> SEQUENCE: 46

| | | | | | |
|---|---|---|---|---|---|
| atggcttcca | ttacaggctc | atcagctacc | gccatgtcct | gctccttcaa | ggcacctaac | 60 |
| cgtgtatcga | atttgaaaac | atcttctctt | tcattcaagg | ggattagcta | ctcttccatc | 120 |
| agtgtgaatc | cagccactcg | tcgcctcagt | attacttgtg | cggctaagcc | agagactgtc | 180 |
| aacaaagtgt | gtgacattgt | gaagaaacaa | ctggctcttt | ctgctgatac | tgatgtctgt | 240 |
| ggagattcaa | agtttgctgc | gcttggtgct | gattctcttg | atacggtgga | gattgtcatg | 300 |
| ggacttgagg | aagaatttgg | catctcggtg | gaagaagaca | gtgctcagag | tattgcaacc | 360 |
| gttcaagatg | ctgcagacct | gattgaggat | ctcatttcaa | agaaagcttg | a | 411 |

<210> SEQ ID NO 47
<211> LENGTH: 136
<212> TYPE: PRT
<213> ORGANISM: Lycopersicon esculentum

<400> SEQUENCE: 47

```
Met Ala Ser Ile Thr Gly Ser Ser Ala Thr Ala Met Ser Cys Ser Phe
1               5                   10                  15

Lys Ala Pro Asn Arg Val Ser Asn Leu Lys Thr Ser Ser Leu Ser Phe
            20                  25                  30

Lys Gly Ile Ser Tyr Ser Ser Ile Ser Val Asn Pro Ala Thr Arg Arg
        35                  40                  45

Leu Ser Ile Thr Cys Ala Ala Lys Pro Glu Thr Val Asn Lys Val Cys
    50                  55                  60

Asp Ile Val Lys Lys Gln Leu Ala Leu Ser Ala Asp Thr Asp Val Cys
65                  70                  75                  80

Gly Asp Ser Lys Phe Ala Ala Leu Gly Ala Asp Ser Leu Asp Thr Val
                85                  90                  95

Glu Ile Val Met Gly Leu Glu Glu Phe Gly Ile Ser Val Glu Glu
            100                 105                 110

Asp Ser Ala Gln Ser Ile Ala Thr Val Gln Asp Ala Ala Asp Leu Ile
            115                 120                 125

Glu Asp Leu Ile Ser Lys Lys Ala
        130                 135
```

<210> SEQ ID NO 48
<211> LENGTH: 411
<212> TYPE: DNA
<213> ORGANISM: Solanum tuberosum

<400> SEQUENCE: 48

```
atggcttcta ttacaggctc atcagctacc gccatgtcct gctccttcaa ggaacttgac      60
cgtgtctcga atttgaagac atcttctctt tcattcaagg ggattagcta ctcttccatc     120
agagtgaatc cagccactcg tcgcctcagt attacttgtg cggctaagcc agagactgtc     180
aacaaagtgt gtgacattgt gaagaaacaa ctggctctct ctgctggtac tgaagtctgt     240
ggagaatcaa agtttgctgc gcttggtgct gattctcttg ataccggtgga gattgtcatg     300
ggacttgagg aagagtttgg catctccgtg gaagaagaca gtgctaacag tattgcaaca     360
gttcaagatg ctgcagacct gattgaggat ctcatttcaa agaaagcttg a              411
```

<210> SEQ ID NO 49
<211> LENGTH: 136
<212> TYPE: PRT
<213> ORGANISM: Solanum tuberosum

<400> SEQUENCE: 49

```
Met Ala Ser Ile Thr Gly Ser Ser Ala Thr Ala Met Ser Cys Ser Phe
1               5                   10                  15

Lys Ser Leu Asp Arg Val Ser Asn Leu Lys Thr Ser Ser Leu Ser Phe
            20                  25                  30

Lys Gly Ile Ser Tyr Ser Ser Ile Arg Val Asn Pro Ala Thr Arg Arg
        35                  40                  45

Leu Ser Ile Thr Cys Ala Ala Lys Pro Glu Thr Val Asn Lys Val Cys
    50                  55                  60

Asp Ile Val Lys Lys Gln Leu Ala Leu Ser Ala Gly Thr Glu Val Cys
65                  70                  75                  80
```

```
Gly Glu Ser Lys Phe Ala Ala Leu Gly Ala Asp Ser Leu Asp Thr Val
                85                  90                  95

Glu Ile Val Met Gly Leu Glu Glu Glu Phe Gly Ile Ser Val Glu Glu
            100                 105                 110

Asp Ser Ala Asn Ser Ile Ala Thr Val Gln Asp Ala Ala Asp Leu Ile
        115                 120                 125

Glu Asp Leu Ile Ser Lys Lys Ala
    130                 135

<210> SEQ ID NO 50
<211> LENGTH: 411
<212> TYPE: DNA
<213> ORGANISM: Solanum chacoense

<400> SEQUENCE: 50
atggcttcta ttacaggctc atcagctacc gccatgtcct gctccttcaa ggaacttaac      60
cgtgtctcga atttgaagac atcttctctt tcattcaagg ggattagcta ctcttccatc    120
agagtgaatc cagccactcg tcgcctcagt attacttgtg cggctaagcc agagactgtc    180
aacaaagtgt gtgacattgt gaagaaacaa ctggctcttt ctgctgatac tgaagtctgt    240
ggagattcaa agtttgctgc gcttggtgct gattctcttg atacggtgga gattgtcatg    300
ggacttgagg aagagtttgg catctccgtg gaagaagata tgctcagag tattgcaaca     360 gttcaagatg ctgcagacct gattgaggat ctcatttcaa agaaagcttg a             411

<210> SEQ ID NO 51
<211> LENGTH: 136
<212> TYPE: PRT
<213> ORGANISM: Solanum chacoense

<400> SEQUENCE: 51

Met Ala Ser Ile Thr Gly Ser Ser Ala Thr Ala Met Ser Cys Ser Phe
1               5                   10                  15

Lys Glu Leu Asn Arg Val Ser Asn Leu Lys Thr Ser Ser Leu Ser Phe
            20                  25                  30

Lys Gly Ile Ser Tyr Ser Ser Ile Arg Val Asn Pro Ala Thr Arg Arg
        35                  40                  45

Leu Ser Ile Thr Cys Ala Ala Lys Pro Glu Thr Val Asn Lys Val Cys
    50                  55                  60

Asp Ile Val Lys Lys Gln Leu Ala Leu Ser Ala Asp Thr Glu Val Cys
65                  70                  75                  80

Gly Asp Ser Lys Phe Ala Ala Leu Gly Ala Asp Ser Leu Asp Thr Val
                85                  90                  95

Glu Ile Val Met Gly Leu Glu Glu Glu Phe Gly Ile Ser Val Glu Glu
            100                 105                 110

Asp Ser Ala Gln Ser Ile Ala Thr Val Gln Asp Ala Ala Asp Leu Ile
        115                 120                 125

Glu Asp Leu Ile Ser Lys Lys Ala
    130                 135

<210> SEQ ID NO 52
<211> LENGTH: 417
<212> TYPE: DNA
<213> ORGANISM: Nicotiana tabacum

<400> SEQUENCE: 52
atggcttcta ttacaggttc atctgttacc atgtcatgct ccttgaagca aaatcaggca      60
```

```
cttaaccgag tctctaattt gaagacgtct tctctttcat tcaaggggat aagcttccct    120
tccattcgat tgaatcgagc cactggccac ctcactatca cttgcgcggc taagccagaa    180
acggtcaaca aggtgtgtga aattgtgaag aaacaactgg ctctttctgg tgaaactgaa    240
gtcagtggag agtcaaagtt tgctgcgctt ggtgctgatt ctcttgatac ggtggagata    300
gtcatggggc ttgaggaaga gtttggtatt ccgtagaag aagacagtgc tcagagtatt     360
gcaacagttc aagatgctgc agacctgatt gaggatctca tttcaaagaa agcttga       417
```

<210> SEQ ID NO 53
<211> LENGTH: 138
<212> TYPE: PRT
<213> ORGANISM: Nicotiana tabacum

<400> SEQUENCE: 53

Met Ala Ser Ile Thr Gly Ser Ser Val Thr Met Ser Cys Ser Leu Lys
1               5                   10                  15

Gln Asn Gln Ala Leu Asn Arg Val Ser Asn Leu Lys Thr Ser Ser Leu
            20                  25                  30

Ser Phe Lys Gly Ile Ser Phe Pro Ser Ile Arg Leu Asn Arg Ala Thr
        35                  40                  45

Gly His Leu Thr Ile Thr Cys Ala Ala Lys Pro Glu Thr Val Asn Lys
    50                  55                  60

Val Cys Glu Ile Val Lys Lys Gln Leu Ala Leu Ser Gly Glu Thr Glu
65                  70                  75                  80

Val Ser Gly Glu Ser Lys Phe Ala Ala Leu Gly Ala Asp Ser Leu Asp
                85                  90                  95

Thr Val Glu Ile Val Met Gly Leu Glu Glu Glu Phe Gly Ile Ser Val
            100                 105                 110

Glu Glu Asp Ser Ala Gln Ser Ile Ala Thr Val Gln Asp Ala Ala Asp
        115                 120                 125

Leu Ile Glu Asp Leu Ile Ser Lys Lys Ala
    130                 135

<210> SEQ ID NO 54
<211> LENGTH: 408
<212> TYPE: DNA
<213> ORGANISM: Petunia hybrida

<400> SEQUENCE: 54

```
atggcttcta ttactgcctc atcccttgc tccttaagc caaatcatgc acttaaccga     60
gtctctaatt tgaagacgtc gtctcttact ttcaagggga taagtttctc ttccatcaga   120
ttgattccaa ctactcgtcg cctctgtatt acttgcgcgg ctaagccaga gacagtaaat   180
aaagtgtgtg aaattgtgaa gaaacagctg gctctttctg ctgattctga agtcagtgga   240
gagtcaaagt tgctgcgct tggtgctgat tctcttgata cggtggaaat tgtcatggga   300
cttgaggaag agttcggtat ttccgtggaa aagatagtgc tcagagtat tgcaacagtt   360 caagatgctg cagacctgat tgaggatctc atttcaaaga aagcttga              408
```

<210> SEQ ID NO 55
<211> LENGTH: 135
<212> TYPE: PRT
<213> ORGANISM: Petunia hybrida

<400> SEQUENCE: 55

Met Ala Ser Ile Thr Ala Ser Ser Leu Cys Ser Phe Lys Pro Asn His

```
1               5                  10                 15
Ala Leu Asn Arg Val Ser Asn Leu Lys Thr Ser Ser Leu Thr Phe Lys
            20                 25                 30

Gly Ile Ser Phe Ser Ser Ile Arg Leu Ile Pro Thr Thr Arg Arg Leu
            35                 40                 45

Cys Ile Thr Cys Ala Ala Lys Pro Glu Thr Val Asn Lys Val Cys Glu
            50                 55                 60

Ile Val Lys Lys Gln Leu Ala Leu Ser Ala Asp Ser Glu Val Ser Gly
 65                 70                 75                 80

Glu Ser Lys Phe Ala Ala Leu Gly Ala Asp Ser Leu Asp Thr Val Glu
            85                 90                 95

Ile Val Met Gly Leu Glu Glu Glu Phe Gly Ile Ser Val Glu Glu Asp
            100                105                110

Ser Ala Gln Ser Ile Ala Thr Val Gln Asp Ala Ala Asp Leu Ile Glu
            115                120                125

Asp Leu Ile Ser Lys Lys Ala
            130                135
```

<210> SEQ ID NO 56
<211> LENGTH: 411
<212> TYPE: DNA
<213> ORGANISM: Capsicum annum

<400> SEQUENCE: 56

```
atggcttcta tcacaggctc atccatctcc tcctccttca aacttaatca ggcacttaac    60
cgtgtctgtt gtttgaagac accttctatt tctttcaagg ggataagctt gtcttccagc   120
agattgaatc aagccactcg tcgcctcagt attacttgtg cggctaaacc agagactgtc   180
aacaaagtgt gtgacattgt gaagaaacaa ctggctcttt ccgctgatac tgcagttttgt   240
ggagagtcca gtttgctgc gcttggtgct gattctcttg atacggtgga gattgtcatg   300
ggacttgagg aagagtttgg catctccgtg gaagaagata gtgctcagaa tattgcaaca   360
gttcaagatg ctgcagacct gattgaggat ctcatttcaa agaatgcttg a            411
```

<210> SEQ ID NO 57
<211> LENGTH: 136
<212> TYPE: PRT
<213> ORGANISM: Capsicum annum

<400> SEQUENCE: 57

```
Met Ala Ser Ile Thr Gly Ser Ser Ile Ser Ser Ser Phe Lys Leu Asn
 1               5                  10                 15

Gln Ala Leu Asn Arg Val Cys Cys Leu Lys Thr Pro Ser Ile Ser Phe
            20                 25                 30

Lys Gly Ile Ser Leu Ser Ser Ser Arg Leu Asn Gln Ala Thr Arg Arg
            35                 40                 45

Leu Ser Ile Thr Cys Ala Ala Lys Pro Glu Thr Val Asn Lys Val Cys
            50                 55                 60

Asp Ile Val Lys Lys Gln Leu Ala Leu Ser Ala Asp Thr Ala Val Cys
 65                 70                 75                 80

Gly Glu Ser Lys Phe Ala Ala Leu Gly Ala Asp Ser Leu Asp Thr Val
            85                 90                 95

Glu Ile Val Met Gly Leu Glu Glu Glu Phe Gly Ile Ser Val Glu Glu
            100                105                110

Asp Ser Ala Gln Asn Ile Ala Thr Val Gln Asp Ala Ala Asp Leu Ile
            115                120                125
```

Glu Asp Leu Ile Ser Lys Asn Ala
    130                 135

<210> SEQ ID NO 58
<211> LENGTH: 638
<212> TYPE: DNA
<213> ORGANISM: Lycopersicon esculentum

<400> SEQUENCE: 58

| | | | | | |
|---|---|---|---|---|---|
| gggattactt | gagtccgcta | atggagttca | tgacttcact | tcctgttgat | gaaaaaatag | 60 |
| ttcttgttgg | ccatagcgtt | ggtggactcg | ccatttctaa | agccatggaa | accttccctg | 120 |
| aaaagatttc | tgttgctgta | tttcttagtg | gtgtaatgcc | tggtccaaat | attagtgcat | 180 |
| caatcgtcta | tactgaggca | atcaatgcaa | taatacgtga | acttgataat | cgggttacat | 240 |
| accacaacgg | atctgagaat | cctccaacga | ccttcaacct | aggtcccaag | ttcttggaaa | 300 |
| ctaatgctta | ccatctgagc | ccaattgagg | atttggcgct | ggctactaca | ctagtaaggc | 360 |
| cattttattt | atacagtgcg | gaagatgttt | ctaaagagat | agtactttca | agcaaaaaat | 420 |
| atggatcagt | taagagagtg | ttcatctttg | ctgctaaaaa | tgaagttgtg | aagaaggaat | 480 |
| ttttccaaac | gatgattgaa | aagaatccac | caaatgaaat | agaagtaatc | gagggtctg | 540 |
| accatgcgac | catgacgtct | aagccccaac | agctttatac | tactcttctc | aacattgcca | 600 |
| acaagtatac | ctgagccctt | tcaatttgat | atttcatc | | | 638 |

<210> SEQ ID NO 59
<211> LENGTH: 1281
<212> TYPE: DNA
<213> ORGANISM: Solanum tuberosum

<400> SEQUENCE: 59

| | | | | | |
|---|---|---|---|---|---|
| caattgtcta | acaagtcttg | ttgttctaat | acttgtcctg | ccatatgtaa | atgcaacctt | 60 |
| gtcaaggcca | aaagctgcaa | agcactttgt | gttggttcat | aaggcatgtc | atggagcctg | 120 |
| gtcttggtac | aaaattatag | cattgatgaa | atcttcaggg | cataatgtca | cagctcttga | 180 |
| cttaggtgct | tctggaatca | actcgaaaca | ggcccccgaa | atcacacatt | tttctgattt | 240 |
| catgagtcct | ttaatcgagt | tcatgacttc | tcttcctgca | cataaaaatg | ttgttcttgt | 300 |
| tggccatagc | attggtggtc | tagccatttc | gaaagccatg | gaacttttc | cagaaaagat | 360 |
| ttcaggtgct | gtatttgtag | ctggtctaat | gcctggtcca | aatatcaatg | caagcactgt | 420 |
| ctacattgag | ttatgcaatg | cagtagtatc | gaaacttgat | aatcgtgtta | taccataa | 480 |
| tgggacttcg | aatcctccaa | ccttcatttt | aggtccgaag | tacttagcaa | gtaatgttta | 540 |
| ccaacagagc | ccaattgagg | atttggcgtt | ggccactaca | ctagtaaggg | aaatattttt | 600 |
| ttacagtgtg | gaggatgttt | ctaaggagat | aattctttcg | agaaaaagat | atggatcaat | 660 |
| taggcgagcg | tttgttgtta | ctccggaaga | taaacttcta | aaaaggaat | tcaacaattg | 720 |
| atgattgaca | gaaatccacc | ttgatgaagt | gaaagagatc | caagggcgct | gaccataatg | 780 |
| gccatgatgt | ctaaggcccc | atgaactttt | ttaacatttc | ttctgagatt | tgctgacaag | 840 |
| ggacttactc | acgtgtctgt | tgcatctggt | ttgacgaacc | taagttctt | tccatggaaa | 900 |
| gtccttcccg | agctaagttg | gaattggaat | gtcccaattc | attttccttc | aagttggtcg | 960 |
| caggttccct | tcaatgggga | ctaattaggg | ctggggaatg | cacgtcctta | aacgattttt | 1020 |
| tttcccgata | aaaagaaga | gaggaacgaa | cgaaaatcgc | ggggggggcg | cggggaccca | 1080 |
| aattccgact | aaaatggagg | aagttttaaa | cggcgcgcaa | gaggcgggtt | aaaaccgtcg | 1140 |

```
gctcggaaga caccggggtt cccacaataa ggcttgggag agacaccttt tcgcaggggt    1200
taagaaaaga cccggtcct ctcaagaagg acgtcagaga ggaaggccgc ttgacaaaca    1260
ccgggtcgtt ggcaccacgc a                                              1281

<210> SEQ ID NO 60
<211> LENGTH: 729
<212> TYPE: DNA
<213> ORGANISM: Nicotiana tabacum
<220> FEATURE:
<221> NAME/KEY: unsure
<222> LOCATION: (1)..(729)
<223> OTHER INFORMATION: unsure at all n locations

<400> SEQUENCE: 60
aaaaaaagat atggagaaaa gcaagtttct aacaagtcta gttctaatac tttgttttca      60
tatgtaaatg caacaacatc agtgactata tggcctaagg cgagcaagca tttcgtgcta     120
gttcacgggg cttgccatgg agcttggtct tggtacaaga ttatggcgtc gttaaaaact     180
tcaggacata atgtcacagc tctggactta ggtgcttcgg gagtcaaccc aaagcagggc     240
cttgaaatcc cacatttatc ggactacgtt agtccgctaa tgaagttcat ggcttctctt     300
cctgcagatg aaaaagtgat tcttgtaggt catagccttg gtgatttgc catttctaaa     360 gcgatggaaa cttttccaga aaagatttca gttgctgtat ttgtcactgc tctaatgcct     420
ggtccaactc tcaatgcaac caccatattt attgagtcat ccaaggcagc aatatcagta     480
cttgataatc gtgttacatt cgatagtgga cctatgaatc ctccaacaac cttcagcttt     540
ggtccgaagt acttggcgag ttatctttat ccactgagcc caattcagga ctgggcactg     600
gctactacag tagtaaggcc attatatttta tacagttcgg atgacatatc aaaggaaata     660 gttcttttcaa gcaaaaagta tgcatcagtt taacgagtgt tccttgtggt ggtgaanata    720
aagtctaaa                                                             729

<210> SEQ ID NO 61
<211> LENGTH: 719
<212> TYPE: DNA
<213> ORGANISM: Capsicum annum

<400> SEQUENCE: 61
ggcacgagga agatatggaa aaagcaagt ttctaacaag tctagttcta atacttctgt       60
tgtcatatgt aaatgcaaca acatcaggcc ctaaatggcc taaagctcgt aagcactttg     120
tgctagttca tggggcttgc catggagcct gggcttggta caagataata gcatcgataa     180
aaacttcagg gcataacgta acagctctgg acttgggtgc ttcagggtc aacccaaaac      240 aggtccttga atcccacat ttatcggatt actttagtcc gctaatggag ttcatgactt      300
ctcttccaac agatgaaaaa gtgattcttg ttggtaacag tcttggtgga tttgccattg     360
ctaaagctat ggaaatcttt cctgagaaga tttcagttgc tgtatttgtc gctgctctca     420
tgcctggtct aattctcgat gcggccacca tctataatga acatccagc ggaacattta      480 tacttgataa tcttattaca ttcgataatg gacctaccaa tcctccaaca accgtcagct     540
ttggtccgaa gttcttggcg agttatattt atccactgag cccaattcaa gactgggcac     600
tggctacgac actagtaagg ccattgtatc tttacagttt ggatgacata tcaaaggaga     660
tggttcttac aagcaagaag tatggatcag ttaggcgagc atatatggtg gcggctgaa     719

<210> SEQ ID NO 62
```

```
<211> LENGTH: 588
<212> TYPE: DNA
<213> ORGANISM: Arabidopsis thaliana

<400> SEQUENCE: 62
ggtaccatct tctgtatcat cttcttcttc ttcaaggtga gtctctagat ccgttcgctt      60
gattttgctg ctcgttagtc gttattgttg attctctatg ccgatttcgc tagatccgtt     120
tagcatgcgt tgtggtttta tgagaaaatc tttgttttgg gggttgcttg ttatgtgatt     180
cgatccgtgc ttgttggatc gatctgagct aattcttaag gtttatgtgt tagatcaatg     240
gagtttgagg attcttctcg cttctgtcga tctctcgctg ttattttttgt tttttttcagt     300 gaagtgaagt tgtttagttc gaaatgactt cgtgtatgct cgattgatct ggttttaatc     360
ttcgatctgt taggtgttga tgtttacaag tgaattgatg tgttttctcg ttgtgatctg     420
tgaagtttga acctagtttt ctcaataatc aacatatgaa gcgatgtttg agtttcaata     480
aacgctgcta atcttcgaaa ctaagttgtg atctgattcg tgtttacttc atgagcttat     540
ccaattcatt tcggtttcat tttactttt ttttagtgaa ggcgcgcc                   588
```

US 9,006,517 B2

METHODS AND COMPOSITIONS FOR PLANT PEST CONTROL

CROSS REFERENCE TO RELATED APPLICATIONS

This application claims the priority of U.S. Provisional Application Ser. No. 61/027,473, filed Feb. 10, 2008, the entire disclosure of which is incorporated herein by reference.

INCORPORATION-BY-REFERENCE OF SEQUENCE LISTING IN COMPUTER READABLE FORM

The Sequence Listing, which is a part of the present disclosure, includes a computer readable form 96 KB file entitled "MNDI005WOsequence" comprising nucleotide sequences of the present invention submitted via EFS-Web. The subject matter of the Sequence Listing is incorporated herein by reference in its entirety.

BACKGROUND OF THE INVENTION

1. Field of the Invention

The present invention relates to methods and compositions for pest or pathogen control in plants. More particularly, it discloses transgenic plant cells, plants and seeds comprising recombinant DNA and methods of making and using such plant cells, plants and seeds that are associated with pest resistance.

2. Description of Related Art

Plants and animals are targets for infection by many nematode pests. Improved methods for protecting plants from nematode infection are therefore desired since they would increase the amount and stability of food production.

There are numerous plant-parasitic nematode species, including various cyst nematodes (e.g. *Heterodera* spp.), root knot nematodes (e.g. *Meloidogyne* spp.), lesion nematodes (e.g. *Pratylenchus* spp.), dagger nematodes (e.g. *Xiphinema* spp.) and stem and bulb nematodes (e.g. *Ditylenchus* spp.), among others. Tylenchid nematodes (members of the order Tylenchida), including the families Heteroderidae, Meloidogynidae, and Pratylenchidae, are the largest and most economically important group of plant-parasitic nematodes. Other important plant-parasitic nematodes include Dorylaimid nematodes (e.g. *Xiphinema* spp.), among others. Nematode species grow through a series of lifecycle stages and molts. Typically, there are five stages and four molts: egg stage; J1 (i.e. first juvenile stage); M1 (i.e. first molt); J2 (second juvenile stage; sometimes hatch from egg); M2; J3; M3; J4; M4; A (adult). Juvenile ("J") stages are also sometimes referred to as larval ("L") stages. Gene expression may be specific to one or more lifecycle stages. Nematodes have evolved as very successful parasites of both plants and animals and are responsible for significant economic losses in agriculture and livestock and for morbidity and mortality in humans. Nematode parasites of plants can inhabit all parts of plants, including roots, developing flower buds, leaves, and stems. Plant parasites are classified on the basis of their feeding habits into the broad categories migratory ectoparasites, migratory endoparasites, and sedentary endoparasites. Sedentary endoparasites, which include the root knot nematodes (*Meloidogyne* species, RKN), cyst nematodes (*Globodera* and *Heterodera* species) and reniform nematodes (*Rotylenchulus* species) induce feeding sites and establish long-term infections within roots that are often very damaging to crops. Nematode infection is a significant problem in the farming of many agriculturally significant crops. For example, soybean cyst nematode (*Heterodera glycines*, SCN) is believed to be responsible for yield losses in soybeans estimated to be in excess of $1 billion per year in North America. Such damage is the result of the stunting of the soybean plant caused by the cyst nematode. The stunted plants have smaller root systems, show symptoms of mineral deficiencies in their leaves, and wilt easily. It is estimated that parasitic nematodes cost the horticulture and agriculture industries in excess of $78 billion worldwide a year, based on an estimated average 12 percent annual loss spread across all major crops.

Traditional approaches for control of plant diseases have been the use of chemical treatment and the construction of interspecific hybrids between resistant crops and their wild-type relatives as sources of resistant germplasm. Chemical nematode control agents are not effective in eradicating nematode infestations. Because of the lack of selectivity, the chemical nematode control agents exert their effects on non-target fauna as well, often effectively sterilizing a field for a period of time following the application of nematode control agents. Nematicides such as Aldicarb and its environmental breakdown products are known to be highly toxic to mammals. As a result, government restrictions have been imposed on the use of these chemicals. The most widely used nematicide, methyl bromide, is scheduled to be soon retired from use, and at present, there is no promising candidate to replace this treatment.

Methods employing plant biotechnology have provided effective means to control insect infestations, for instance through plant expression of an insect control agent. Biotechnologically-related nematode control agents have generally been reported to be nucleotides expressed by a plant that are selectively toxic to the target nematode when ingested by the nematode. However, there are few examples of effectively applied biotechnology methods to control nematode infection.

SUMMARY OF THE INVENTION

In one aspect, the invention provides agents effective as a plant nematode control agent. The effective compounds are, in one embodiment, methylketones not previously known to be toxic to plant parasitic nematodes. Additionally, the inventors have developed compositions and methods to express methylketones, such as 2-undecanone, 2-tridecanone and 2-pentadecanone, in the roots of plants that nematodes infect, to reduce or inhibit nematode growth, development, or the plant disease caused by nematode infection. In particular embodiments the method comprises production of transgenic plants containing one or more transgenes that provide for the production of 2-undecanone, 2-tridecanone and/or 2-pentadecanone in plant tissues susceptible to nematode infection.

In another aspect, the invention provides methods for construction and use of a transgene expression cassette comprising a methylketone synthase coding region and expression of the synthase in a plant cell, particularly the root cells of a plant. The invention provides for a transgenic plant comprising the transgene wherein the roots of the transgenic plant produce a methylketone. The methylketone synthase transgene, in certain embodiments, additionally comprises a sequence region comprising a heterologous plastid transit peptide molecule in operable linkage to the methylketone synthase coding region. By "heterologous" it is meant that a given sequence is not in its native context with respect to any other referenced sequence. Thus one sequence may be heterologous with respect to second, operably linked, sequence where both sequences can be isolated from the same species, but will be not be in their native orientation. A heterologous transit peptide operably linked to a given methylketone synthase coding region is therefore not a transit peptide normally found in nature in an unmodified state in operable linkage to the methylketone synthase coding region.

In yet another aspect of the invention, modified DNA coding sequences comprising SEQ ID NO: 1 or 2 are provided that encode a methylketone synthase of SEQ ID NO: 3; SEQ ID NO: 4 is provided encoding the methylketone synthase of SEQ ID NO: 5; and SEQ ID NO: 6 is provided encoding the methylketone synthase SEQ ID NO: 7. In certain embodiments, the DNA coding sequence encoding a polypeptide with methylketone synthase activity shares at least about 80%, 85%, 90%, 95%, 98%, or 99% percent sequence identity to any one or more of said SEQ ID NOs.

In still yet another aspect of the invention, a heterologous fusion protein is provided that comprises a plastid transit peptide molecule (such as SEQ ID NO: 9 or 11) and a methylketone synthase molecule (such as SEQ ID NO: 13, 15, 17, 19, 21, 23, 25 or 27) or methylketone synthase molecule variant (such as SEQ ID NO: 29, 31, 33, 35, 37, or 39) with methylketone synthase activity, or a methylketone synthase molecule having at least about 80%, 85%, 90%, 95%, 98%, or 99% percent sequence identity to any one or more of said SEQ ID NOs.

In still yet another aspect of the invention, a transgene expression cassette is provided comprising a heterologous acyl carrier protein coding region that encodes for an acyl carrier protein (such as SEQ ID NO: 41, 43, 45, 47, 49, 51, 53, 55, or 57) that is expressed in plant tissues with the transgene comprising the methylketone synthase coding region.

In still yet another aspect of the invention, a transgenic seed is provided comprising a heterologous plastid transit peptide molecule in operable linkage to the methylketone synthase coding region. The transgenic seed may additionally comprise a transgene expression cassette comprising a heterologous acyl carrier protein coding region.

Other aspects of the invention are specifically directed to transgenic plant cells, and transgenic plants comprising a plurality of the plant cells, nuclei and organelles, and progeny transgenic seed, embryo, ovule and transgenic pollen from such plants. A plant cell and parts thereof is selected from a population of transgenic plant cells transformed with a heterologous methylketone synthase coding region and may additionally comprise a heterologous acyl carrier protein coding region by selecting the transgenic plant cell from any population comprising the heterologous coding region as compared to a cell that does not have the heterologous coding region.

This invention also provides methods for manufacturing non-natural, transgenic seed that can be used to produce a crop of transgenic plants with pest resistance resulting from expression of a heterologous methylketone synthase coding region and in certain embodiments the co-expression of a heterologous acyl carrier protein coding region in the nucleus or organelle or cytoplasm of the plant cells making up the transgenic plants. The various aspects of this invention are especially useful for transgenic plants having nematode resistance activity that include, without limitation, cereals including corn, wheat, barley, rye, and rice; vegetables; tomatoes; potatoes; clovers; legumes including beans, soybeans, peas and alfalfa; sugar cane; sugar beets; tobacco; cotton; rapeseed (canola); sunflower; safflower; and sorghum.

The present invention provides for a transgenic soybean plant comprising within its genome a heterologous methylketone synthase coding region and may additionally comprise a heterologous acyl carrier protein coding region, wherein the plant is resistant to nematode infection or displays reduced disease symptoms caused by nematode infection.

The present invention further provides a method of increasing the yield of a nematode tolerant crop plant. The method comprises growing a crop plant comprising a heterologous methylketone synthase coding region which may additionally comprise a heterologous acyl carrier protein coding region in the presence of nematodes.

Another aspect of the invention provides a method of producing a hybrid seed comprising acquiring hybrid seed from a nematode tolerant plant which also has a stably-integrated heterologous nucleotide sequence encoding a methylketone synthase and may also have integrated a heterologous nucleotide sequence encoding an acyl carrier protein. The method further comprises producing a crop from plants grown from the hybrid seed, wherein a fraction of the plants produced from said hybrid seed are homozygous for the heterologous methylketone synthase coding sequence and if present, the heterologous acyl carrier protein coding sequence, a fraction of the plants produced from said hybrid seed are hemizygous for the heterologous methylketone synthase coding sequence and if present, the heterologous acyl carrier protein coding sequence, and a fraction of the plants produced from the hybrid have no heterologous methylketone synthase coding sequence or heterologous acyl carrier protein coding sequence; selecting plants which are homozygous and hemizygous; collecting seed from the selected plants, and planting the seed to produce further progeny plants; repeating the selecting and collecting steps at least once from these progeny plants to produce an inbred line; and crossing the inbred line with a second line to produce hybrid seed. The plants of the invention are selected, without limitation, from the group of corn (maize), soybean, cotton, canola (rape), wheat, sunflower, sorghum, alfalfa, barley, millet, rice, tobacco, tomato, potato, fruit and vegetable crops, turfgrass, sugar cane, sugar beets, and safflower.

In a further aspect of the invention, control of agronomically important soil inhabiting insects is contemplated, which include, but are not limited to *Diabrotica, Diaprepes, Pachnaeus, Asynonychus, Lycoriella, Sciara, Stenophlus*, and *Bradysia* among others. Broader acaricidal, insecticidal, and pest repellent properties are also contemplated.

DETAILED DESCRIPTION OF THE INVENTION

The invention relates to methods and compositions for pest control in plants, in particular nematode control. In one aspect, the invention relates to controlling, preventing or treating nematode infection in transgenic plants. The method comprises, in one embodiment, generation of transgenic plant containing a recombinant construct and expression of such construct to impart nematode resistance to plants. The recombinant construct may comprise a nucleotide sequence encoding one or more proteins, wherein the sequence is operably linked to a heterologous promoter functional in a plant cell, and to cells transformed with the recombinant construct. Cells comprising (meaning including but not limited to) the recombinant construct may be prokaryotic or eukaryotic. In particular, they may be plant cells. Plants and seeds derived from such transformed plant cells are also contemplated. The transgenic plants or parts thereof of the present invention, in one embodiment, produce one or more fatty acid compounds for which at least one is 2-tridecanone. 2-tridecanone is the major methylketone (76% of total volatile content) produced in *Lycopersicon hirsutum* (*Solanum habrochaites*) (compared to 21% 2-undecanone, and 3% 2-pentadecanone; Fridman, et al., *Plant Cell* 17:1252-67, 2005). Higher plants synthesize fatty acids via a metabolic pathway involving an acyl carrier protein co-factor (ACP) and a fatty acid synthase (FAS) enzyme complex. The FAS complex consists of about eight separate enzymes that catalyze thirty or more individual reaction steps, all of which, in plants, are located in the plastids.

The present invention provides heterologous molecules that are directed into the plastid of a plant to provide production of a methylketone, especially 2-tridecanone, from the FAS complex, including, but not limited to, nucleotides that encode polypeptides having methylketone synthase activity such as SEQ ID NO:3, SEQ ID NO:5, SEQ ID NO:7, or the amino acid sequence given in GenBank Accession AY701574. In certain embodiments, the polypeptide having methylketone synthase activity (e.g. allowing for production of methylketones such as 2-undecanone, 2-tridecanone, and 2-pentadecanone) may share at least 80%, at least 85%, at least 90%, at least 95%, at least 98%, at least 99%, or 100% sequence identity, to any one or more amino acid sequence(s) set forth in SEQ ID NO:3, SEQ ID NO:5, SEQ ID NO:7, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, or SEQ ID NO:39. The function of the encoded polypeptide may also be determined by measuring the efficacy of the presence of the transgene that encodes it in reducing nematode infection, growth, reproduction, or symptomatology. For instance, a reduction in root galls, cysts, or worm number of 20% or more, 25% or more, 50% or more, 80% or more, or 95% or more, in a transgenic plant comprising a heterologous nucleotide construct encoding methylketone synthase activity, relative to a control plant, for instance an otherwise isogenic plant not comprising the heterologous molecule, under similar conditions, indicates the presence of a functional molecule.

In certain embodiments, a heterologous molecule provided by the present invention that is directed into the plastid of a plant to provide production of a methylketone may share at least 80%, at least 85%, at least 90%, at least 95%, at least 98%, at least 99%, or 100% sequence identity at the nucleotide level with one or more sequence(s) as set forth in SEQ ID NO:1, SEQ ID NO:2, SEQ ID NO:4, SEQ ID NO:6, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:34, SEQ ID NO:36, or SEQ ID NO:38; or any of SEQ ID NOs:58-61. Thus, in particular embodiments, the heterologous molecule may comprise a sequence encoding a heterologous chloroplast transit peptide, for instance, without limitation, as shown in SEQ ID NO:9 or SEQ ID NO:11.

Likewise, in certain embodiments, a nucleotide of the present invention may further comprise a sequence that encodes an acyl carrier protein (e.g. ACP1), as set forth in any of SEQ ID NO:41, SEQ ID NO:43, SEQ ID NO:45, SEQ ID NO:47, SEQ ID NO:49, SEQ ID NO:51, SEQ ID NO:53, SEQ ID NO:55, or SEQ ID NO:57, or may comprise a sequence that encodes an acyl carrier protein with at least about 85%, 90%, 95%, 98%, or 99% sequence similarity to any of these sequences.

Yet another aspect of the invention provides methods for production and for use of one or more methylketone(s), such as 2-tridecanone, to control nematode infestation. Thus, methods for production of a methylketone, for instance in a plant cell, are provided. The methylketone may then be applied to soil prior to, during, or subsequent to planting of a crop, in order to control or reduce nematode infestation or symptomatology of crop plants grown in that soil.

Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994. The nomenclature for DNA bases as set forth at Title 37 of the United States Code of Federal Regulations, Part 1, section 1.822.

As used herein, a "transgenic plant" is any plant in which one or more, or all, of the cells of the plant include a transgene. A transgene may be integrated within a nuclear genome or organelle genome, or it may be extra-chromosomally replicating DNA. The term "transgene" means a nucleic acid that is partly or entirely heterologous, foreign, to a transgenic microbe, plant, animal, or cell into which it is introduced. Cells that make up various cell and tissue types of plants include but are not limited to seed, root, leaf, shoot, flower, pollen and ovule.

"Recombinant DNA" is a polynucleotide having a genetically engineered modification introduced through combination of endogenous and/or exogenous molecules in a transcription unit, manipulation via mutagenesis, restriction enzymes, and the like or simply by inserting multiple copies of a native transcription unit. Recombinant DNA may comprise DNA segments obtained from different sources, or DNA segments obtained from the same source, but which have been manipulated to join DNA segments which do not naturally exist in the joined form. An isolated recombinant polynucleotide may exist, for example as a purified molecule, or integrated into a genome, such as a plant cell, or organelle genome or a microbe plasmid or genome. The polynucleotide comprises linked regulatory molecules that cause transcription of an RNA in a plant cell.

As used herein, "percent identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence. "Percent identity" ("% identity") is the identity fraction times 100.

"Expression" means transcription of DNA to produce RNA. The resulting RNA may be without limitation mRNA encoding a protein, antisense RNA, or a double-stranded RNA for use in RNAi technology. Expression also may refer to translation of RNA, i.e. the production of encoded protein from an mRNA.

As used herein, "promoter" means regulatory DNA molecules for initializing transcription. A "plant promoter" is a promoter capable of initiating transcription in plant cells whether or not its origin is a plant cell. For example it is well known that certain *Agrobacterium* promoters are functional in plant cells. Thus, plant promoters include promoter DNA obtained from plants, plant viruses (in particular, double stranded DNA viruses) and bacteria such as *Agrobacterium* and *Bradyrhizobium* bacteria. Constitutive promoters generally provide transcription in most or all of the cells of a plant. In particular, promoters such as the FMV promoter (FMV, U.S. Pat. No. 6,051,753), the enhanced 35S promoter (E35S, U.S. Pat. No. 5,359,142), rice actin promoter (U.S. Pat. No.

5,641,876), and various chimeric promoters (U.S. Pat. No. 6,660,911) are useful in the present invention. Examples of promoters under developmental control include promoters that preferentially initiate transcription in certain tissues, such as leaves, roots, or seeds. Such promoters are referred to as "tissue-preferred". Promoters that initiate transcription only in certain tissues are referred to as "tissue specific."

A number of root-specific or root-enhanced promoters or fragments of such that provide enhanced expression in root tissues relative to other plant tissues have been identified and are known in the art (e.g. U.S. Pat. Nos. 5,110,732, 5,837,848, 5,837,876; 5,633,363; 5,459,252; 5,401,836; 7,196,247; 7,232,940; 7,119,254; and 7,078,589). Examples include root-enhanced or root-specific promoters such as the CaMV-derived as—1 promoter or the wheat POX1 promoter (U.S. Pat. No. 5,023,179), the acid chitinase gene promoter (Samac et al., *Plant Mol. Biol.* 25:587-596 (1994); the root specific subdomains of the CaMV35S promoter (Lam et al., *Proc. Natl. Acad. Sci. (U.S.A.)* 86:7890-7894 (1989); the root-enhanced ORF13 promoter from *Agrobacterium rhizogenes* (Hansen et al., *Mol. Gen. Genet.* 254:337-343 (1997); the promoter for the tobacco root-specific gene RB7 (U.S. Pat. No. 5,750,386); and the root cell-specific promoters reported by Conkling et al. (*Plant Physiol.* 93:1203-1211 (1990). Additional examples include RCc2 and RCc3, promoters that direct root-specific gene transcription in rice (Xu et al., *Plant Mol. Biol.* 27:237, 1995); soybean root-specific glutamine synthetase promoter (Hire et al., *Plant Mol. Biol.* 20:207-218, 1992); root-specific control element in the GRP 1.8 gene of French bean (Keller and Baumgartner, *Plant Cell* 3:1051-1061, 1991); a root-specific promoter of the mannopine synthase (MAS) gene of *Agrobacterium tumefaciens* (Sanger et al., *Plant Mol. Biol.* 14:433-443, 1990); and full-length cDNA clone encoding cytosolic glutamine synthetase (GS), which is expressed in roots and root nodules of soybean (Miao et al., *Plant Cell* 3:11-22, 1991). See also Bogusz et al., *Plant Cell* 2:633-641, 1990, where two root-specific promoters isolated from hemoglobin genes from the nitrogen-fixing non-legume *Parasponia andersonii* and the related non-nitrogen-fixing non-legume *Trema tomentosa* are described. Leach and Aoyagi (1991) describe their analysis of the promoters of the highly expressed rolC and rolD root-inducing genes of *Agrobacterium rhizogenes* (see *Plant Science* (Limerick) 79:69-76). Additional root-preferred promoters include the VfENOD-GRP3 gene promoter (Kuster et al., *Plant Mol. Biol.* 29(4):759-772, 1995); and rolB promoter (Capana et al., *Plant Mol. Biol.* 25:681-691, 1994). Examples of nematode-induced promoters include, for instance, the TobRB7 promoter (Opperman et al., *Science* 263:221-223, 1994), and promoters described in U.S. Pat. Nos. 6,262,344, and 7,193,136.

The term "resistance," or "tolerance" when used in the context of comparing the effectiveness of a transgene in a transgenic plant, refers to the ability of the transgenic plant to maintain a desirable phenotype when exposed to nematode infestation pressures relative to the phenotype presented by a nematode sensitive non-transgenic plant under similar conditions. The level of resistance can be determined by comparing the physical characteristics of the transgenic plant to non-transgenic plants that either have or have not been exposed to nematode infection. Exemplary physical characteristics to observe include plant height, an increase in population of plants that have ability to survive nematode challenge (that is, plants that come in contact with a parasitic nematode may have enhanced root growth, enhanced fruit or grain yield, and reproduction nematode infection or population increase rate). The product of expression of the recombinant DNA may be directly toxic to the nematode (nematicidal) or may affect the mobility, host finding, feeding site establishment, fecundity or have other nematistatic effects.

"Transformed seed" is the seed which has been generated from the transformed plant. A transformed plant contains transformed cells. A transformed cell is a cell that has been altered by the introduction of an exogenous DNA molecule or in the present invention comprises a heterologous methylketone synthase or a heterologous acyl carrier protein or a combination of both.

Nematodes include but are not limited to plant parasitic species, for example, *Heterodera* species, *Globodera* species, *Meloidogyne* species, *Rotylenchulus* species, *Hoplolaimus* species, *Belonolaimus* species, *Pratylenchus* species, *Longidorus* species, *Paratrichodorus* species, *Ditylenchus* species, *Xiphinema* species, *Dolichodorus* species, *Helicotylenchus* species, *Radopholus* species, *Hirschmanniella* species, *Tylenchorhynchus* species, and *Trichodorus* species, and the like.

The present invention provides recombinant DNA constructs comprising a polynucleotide that, when incorporated in a plant cell, imparts to the plant resistance to nematode infection or plant disease caused by the nematode infection. Such constructs also typically comprise a promoter operatively linked to said polynucleotide to provide for expression in the plant cells. Other construct components may include additional regulatory molecules, such as 5' leader regions or 3' untranslated regions (such as polyadenylation sites), intron regions, and transit or signal peptides. Such recombinant DNA constructs can be assembled using methods known to those of ordinary skill in the art.

Recombinant constructs prepared in accordance with the present invention also generally include a 3' untranslated DNA region (UTR) that typically contains a polyadenylation sequence following the polynucleotide coding region. Examples of useful 3' UTRs include but are not limited to those from the nopaline synthase gene of *Agrobacterium tumefaciens* (nos), a gene encoding the small subunit of a ribulose-1,5-bisphosphate carboxylase-oxygenase (rbcS), and the T7 transcript of *Agrobacterium tumefaciens*.

Constructs and vectors may also include a transit peptide for targeting of a protein product, particularly to a chloroplast, leucoplast or other plastid organelle, mitochondria, peroxisome, or vacuole or an extracellular location. For descriptions of the use of chloroplast transit peptides, see U.S. Pat. No. 5,188,642 and U.S. Pat. No. 5,728,925. Many chloroplast-localized proteins are expressed from nuclear genes as precursors and are targeted to the chloroplast by a chloroplast transit peptide (CTP). Examples of other such isolated chloroplast proteins include, but are not limited to those associated with the small subunit (SSU) of ribulose-1,5-bisphosphate carboxylase, ferredoxin, ferredoxin oxidoreductase, the light-harvesting complex protein I and protein II, thioredoxin F, enolpyruvyl shikimate phosphate synthase (EPSPS) and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide, such as, the *Arabidopsis thaliana* EPSPS CTP (CTP2, Klee et al., *Mol. Gen. Genet.* 210:437-442, 1987), and the *Petunia hybrida* EPSPS CTP (CTP4, della-Cioppa et al., *Proc. Natl. Acad. Sci. USA* 83:6873-6877, 1986) has been show to target heterologous EPSPS protein sequences to chloroplasts in transgenic plants. The production of glyphosate tolerant plants by expression of a fusion protein comprising an amino-terminal CTP with a glyphosate resistant EPSPS enzyme is well known by those skilled in the art, (U.S. Pat. No. 5,627,061, U.S. Pat. No. 5,633,435, U.S. Pat. No. 5,312,910, EP 0218571, EP 189707, EP 508909, and EP 924299). Those skilled in the art will recognize that various chimeric constructs can be made that utilize the functionality of a CTP to import various methylketone synthases or acyl carrier proteins into the plant cell plastid.

Stable methods for plant transformation include virtually any method by which DNA can be introduced into a cell, such as by direct delivery of DNA (for example, by PEG-mediated transformation of protoplasts, by electroporation, by agitation with silicon carbide fibers, and by acceleration of DNA coated particles), by *Agrobacterium*-mediated transformation, by viral or other vectors. One preferred method of plant transformation is microprojectile bombardment, for example, as illustrated in U.S. Pat. No. 5,015,580 (soy), U.S. Pat. No. 5,550,318 (maize), U.S. Pat. No. 5,538,880 (maize), U.S. Pat. No. 6,153,812 (wheat), U.S. Pat. No. 6,160,208 (maize), U.S. Pat. No. 6,288,312 (rice) and U.S. Pat. No. 6,399,861 (maize), and U.S. Pat. No. 6,403,865 (maize).

Detailed procedures for *Agrobacterium*-mediated transformation of plants, especially crop plants, include, for example, procedures disclosed in U.S. Pat. Nos. 5,004,863, 5,159,135, 5,518,908, 5,846,797, and 6,624,344 (cotton); U.S. Pat. Nos. 5,416,011, 5,569,834, 5,824,877, 5,914,451 6,384,301, and 7,002,058 (soy); U.S. Pat. Nos. 5,591,616 5,981,840, and 7,060,876 (maize); U.S. Pat. Nos. 5,463,174 and 5,750,871 (*Brassica* species, including rapeseed and canola), and in U.S. Patent Application Publications 2004/0244075 (maize), 2004/0087030 (cotton) and 2005/0005321 (soybean). Additional procedures for *Agrobacterium*-mediated transformation are disclosed in WO9506722 (maize). Similar methods have been reported for many plant species, both dicots and monocots, including, among others, peanut (Cheng et al., *Plant Cell Rep.*, 15:653, 1996); asparagus (Bytebier et al., *Proc. Natl. Acad. Sci. U.S.A.*, 84:5345, 1987); barley (Wan and Lemaux, *Plant Physiol.*, 104:37, 1994); rice (Toriyama et al., *Bio/Technology*, 6:10, 1988; Zhang et al., *Plant Cell Rep.*, 7:379, 1988; wheat (Vasil et al., *Bio/Technology*, 10:667, 1992; Becker et al., *Plant J.*, 5:299, 1994), alfalfa (Masoud et al., *Transgen. Res.*, 5:313, 1996); *Brassica* species (Radke et al., *Plant Cell Rep.*, 11:499-505, 1992); and tomato (Sun et al., *Plant Cell Physiol.*, 47:426-431, 2006). Transgenic plant cells and transgenic plants can also be obtained by transformation with other vectors, such as but not limited to viral vectors (for example, tobacco etch virus (TEV), barley stripe mosaic virus (BSMV), and the viruses referenced in Edwardson and Christie, "The Potyvirus Group: Monograph No. 16", 1991, Agric. Exp. Station, Univ. of Florida), plasmids, cosmids, YACs (yeast artificial chromosomes), BACs (bacterial artificial chromosomes) or any other suitable cloning vector, when used with an appropriate transformation protocol such as but not limited to bacterial infection (for example, with *Agrobacterium* as described above), binary bacterial artificial chromosome constructs, direct delivery of DNA (for example, via PEG-mediated transformation, desiccation/inhibition-mediated DNA uptake, electroporation, agitation with silicon carbide fibers, and microprojectile bombardment). It would be clear to one of ordinary skill in the art that various transformation methodologies can be used and modified for production of stable transgenic plants from any number of plant species of interest. For example the construction of stably inherited recombinant DNA constructs and minichromosomes can be used as vectors for the construction of transgenic plants (U.S. Pat. No. 7,235,716).

Plants of the present invention include, but are not limited to, Acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, cilantro, citrus, clementine, coffee, corn, cotton, cucumber, Douglas fir, eggplant, endive, escarole, eucalyptus, fennel, figs, forest trees, gourd, grape, grapefruit, honey dew, jicama, kiwifruit, lettuce, leeks, lemon, lime, loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini. Crop plants are defined as plants which are cultivated to produce one or more commercial products. Examples of such crops or crop plants include but are not limited to soybean, canola, rape, cotton (cottonseeds), peanut, sunflower, pigeon pea, chickpea, and the like, and grains such as corn, wheat, rice, oat, millet, and rye, and the like. Rape, rapeseed and canola are used synonymously in the present disclosure.

Transformation methods to provide transgenic plant cells and transgenic plants containing stably integrated recombinant DNA are preferably practiced in tissue culture on media and in a controlled environment. Recipient cell targets include but are not limited to meristem cells, callus, immature embryos or parts of embryos, gametic cells such as microspores, pollen, sperm, and egg cells. Any cell from which a fertile plant can be regenerated is contemplated as a useful recipient cell for practice of the invention. Callus can be initiated from various tissue sources, including, but not limited to, immature embryos or parts of embryos, seedling apical meristems, microspores, and the like. Those cells which are capable of proliferating as callus can serve as recipient cells for genetic transformation. Practical transformation methods and materials for making transgenic plants of this invention (for example, various media and recipient target cells, transformation of immature embryos, and subsequent regeneration of fertile transgenic plants) are disclosed, for example, in U.S. Pat. Nos. 6,194,636 and 6,232,526 and U.S. Patent Application Publication 2004/0216189.

In general transformation practice, DNA is introduced into only a small percentage of target cells in any one transformation experiment. Marker genes are generally used to provide an efficient system for identification of those cells that are transformed by a transgenic DNA construct. Preferred marker genes provide selective markers which confer resistance to a selective agent, such as an antibiotic or herbicide. Any of the antibiotics or herbicides to which a plant cell may be resistant can be a useful agent for selection. Potentially transformed cells are exposed to the selective agent. In the population of surviving cells will be those cells where, generally, the resistance-conferring gene is expressed at sufficient levels to permit cell survival in the presence of the selective agent. Cells can be tested further to confirm integration of the recombinant DNA. Commonly used selective marker genes include those conferring resistance to antibiotics such as kanamycin or paromomycin (nptII), hygromycin B (aph IV), gentamycin (aac3 and aacC4) and glufosinate (bar or pat), glyphosate (EPSPS), and dicamba (dicamba monooxygenase). Examples of useful selective marker genes and selection agents are illustrated in U.S. Pat. Nos. 5,550, 318, 5,633,435, 5,780,708, and 6,118,047. Screenable markers or reporters, such as markers that provide an ability to visually identify transformants can also be employed. Non-limiting examples of useful screenable markers include, for example, a gene expressing a protein that produces a detectable color by acting on a chromogenic substrate (for example, beta-glucuronidase, GUS, uidA, or luciferase, luc) or that itself is detectable, such as green fluorescent protein (GFP, gfp) or an immunogenic molecule. Those of skill in the art will recognize that many other useful markers or reporters are available for use.

Trait Stacking and Breeding:

The recombinant DNA constructs of the invention can be stacked with other recombinant DNA for imparting additional agronomic traits (such as in the case of transformed plants, traits including but not limited to herbicide resistance, insect resistance, cold germination tolerance, water deficit tolerance, enhanced yield, enhanced quality, fungal, viral, and bacterial disease resistance) for example, by expressing other transgenes. The recombinant DNA constructs of the present invention can also be transformed into plant varieties that carry natural pest or pathogen resistance genes to enhance the efficacy of the resistance phenotype. Constructs for coordinated decrease and/or increase of gene expression are disclosed in U.S. Patent Application Publication 2004/0126845 A1. Seeds of transgenic, fertile plants can be harvested and used to grow progeny generations, including hybrid generations, of transgenic plants of this invention that include the recombinant DNA construct in their genome. Thus, in addition to direct transformation of a plant with a recombinant DNA construct of this invention, transgenic plants of the invention can be prepared by crossing a first plant having the recombinant DNA with a second plant lacking the construct. For example, the recombinant DNA can be introduced into a plant line that is amenable to transformation to produce a transgenic plant, which can be crossed with a second plant line to introgress the recombinant DNA into the resulting progeny. A transgenic plant of the invention can be crossed with a plant line having other recombinant DNA or naturally occurring genetic regions that confers one or more additional trait(s) (such as, but not limited to, herbicide resistance, pest or disease resistance, environmental stress resistance, modified nutrient content, and yield improvement) to produce progeny plants having recombinant DNA that confers both the desired target sequence expression behavior and the additional trait(s). Typically, in such breeding for combining traits the transgenic plant donating the additional trait is a male line and the transgenic plant carrying the base traits is the female line. The progeny of this cross segregate such that some of the plant will carry the DNA for both parental traits and some will carry DNA for one parental trait; such plants can be identified by markers associated with parental recombinant DNA. Progeny plants carrying DNA for both parental traits can be crossed back into the female parent line multiple times, for example, usually 6 to 8 generations, to produce a progeny plant with substantially the same genotype as one original transgenic parental line but for the recombinant DNA of the other transgenic parental line.

The transgenic plant, plant part, seed or progeny plants of the present invention can be processed into products useful in commerce. These products include but are not limited to meal, flour, oil, hay, starch, juice, protein extract, and fiber.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

The example illustrates the surprising nematicidal efficacy of various methylketones. Methylketones of various chain lengths were tested in vitro against *C. elegans* L1 and L4 larvae and *M. incognita* pre-parasitic J2 larvae, the dispersal larval stage found in the soil. As illustrated in Table 1, nematicidal activity was observed for the medium-length methylketones (10-14 carbon chain lengths). The table shows the in vitro IC30 values (in parts per million) of various methylketones effective against *C. elegans* L1 and L4 larvae and *M. incognita* J2 larvae. IC30 is defined as the concentration of the methylketone at which 30 percent of the nematodes are killed after an exposure of 4 hours for *C. elegans* and 24 hours for *M. incognita*.

TABLE 1

In vitro efficacy of various methylketones on nematodes.

| | C. elegans | | M. incognita |
|---|---|---|---|
| Compound | vs. L1 | vs. L4 | vs. J2 |
| 2-heptanone | >400 | >400 | 400 |
| 2-nonanone | 12.5 | >400 | 200 |
| 2-decanone | 6.3 | >400 | 25 |
| 2-undecanone | 6.3 | 25 | 50 |
| 2-dodecanone | 3.2 | 25 | 50 |
| 2-tridecanone | 3.2 | 12.5 | 50 |
| 2-tetradecanone | 3.2 | >100 | 25 |
| 2-pentadecanone | 12.5 | >100 | 400 |

Whole plant assays were used to determine the efficacy of the methylketones on the infection of soybean plants and tomato plants by nematodes, *H. glycines* and *M. incognita*, respectively. The seeds were planted in 100 percent sand in two-inch square plastic pots and grown to a sufficient size for treatment. Methylketone chemical treatment was applied when the soybean plants showed the first trifoliate beginning to emerge and when the tomato plants reached the 2-3 leaf stage. Following methylketone treatment, nematodes were inoculated into each pot and for soybeans are then incubated for 28 days before harvest and for tomatoes incubated 21 days before harvest.

To each of four pots, five milliliters of the appropriate chemical solution is applied to the surface making sure to avoid contact with the base of the plant. Immediately following the chemical application, the pot surface is wetted sufficiently to water in the chemical. One milligram of chemical per four pots is approximately equivalent to one kilogram per hectare of chemical. A standard test uses four replications. For rates above 2 kg/ha, the desired amount of chemical is weighed into a 30 ml vial (example: 8 kg/ha rate=8 mg chemical in 30 ml vial). The chemical is dissolved in 2 ml of an appropriate solvent, generally acetone. For rates below 2 kg/ha, 2 milligrams of chemistry is weighed into the vial and dissolved in 2 ml of the solvent. The appropriate amount of chemical concentrate is then applied into a separate 30 ml vial and solvent is added to bring the volume to 2 ml (example 0.5 kg/ha=0.5 ml of concentrate+1.5 ml solvent). Each dissolved concentrate is then brought to a total of 20 milliliters using 0.05% Triton X-100 surfactant solution.

Nematode eggs, either SCN or RKN, are added to distilled water to create a concentration of 1000 vermiform eggs per liter of water. At least four hours after chemical treatment the eggs are applied to the treated pots plus non-treated check plants. A small hole about 1 cm deep is punched into the pot surface. One milliliter of the nematode egg slurry is applied into the hole. Immediately afterwards the hole is gently covered. Watering of the test plants is then restricted to a minimum volume needed to prevent wilting for a period of 24 hours. After the 24 hour restricted watering, normal sub-irrigation watering is done for the duration of the test.

The 2-undecanone, 2-tridecanone, and 2-pentadecanone are tested in greenhouse studies against *M. incognita* infection of tomato roots in sand. The tomato plants are commercial varieties sensitive to nematode infection (e.g., Mountain Spring) and do not accumulate the methylketones that are found in the leaf trichomes of some wild tomato species. Shown in Table 2 is a high level of nematicidal activity of various methylketones observed against root knot nematode (*M. incognita*) inoculated into treated pots containing tomato plants. 2-tridecanone is highly effective at controlling nematode-induced galling at both 40 kilograms per hectare (kg/ha) (100% control) and 8 kg/ha (97% control), while 2-undecanone and 2-pentadecanone also demonstrated nematode control. The listed kilograms/hectare (kg/ha) rating is based upon the surface area of the test pots; 1 kg/ha equates to about 1.65 mg compound per kilogram of soil in these assays.

TABLE 2

Activity of various methylketones on root knot nematode disease.

| Compound | Rate (kg/ha) | % Galled Roots | % Control |
| --- | --- | --- | --- |
| 2-undecanone | 40 | 21 | 65% |
| 2-undecanone | 8 | 39 | 35% |
| 2-tridecanone | 40 | 0 | 100% |
| 2-tridecanone | 8 | 2 | 97% |

TABLE 2-continued

Activity of various methylketones on root knot nematode disease.

| Compound | Rate (kg/ha) | % Galled Roots | % Control |
| --- | --- | --- | --- |
| 2-pentadecanone | 40 | 38 | 37% |
| 2-pentadecanone | 8 | 45 | 25% |
| No Compound added | — | 60 | NA |

2-tridecanone was also assayed in the greenhouse for control of soybean cyst nematode (*H. glycines*) in soybeans (Table 3). Nematode control (#cysts/plant) is observed at 40 kg/ha (96% control relative to the non-treated) and 8 kg/ha (80% control relative to the non-treated) when 2-tridecanone was applied as a soil drench prior to nematode inoculation.

TABLE 3

Efficacy of methylketone on cyst nematode infection of soybean

| Compound | Rate (kg/ha) | #cysts/ plant | % Control |
| --- | --- | --- | --- |
| 2-tridecanone | 40 | 2 | 96% |
| 2-tridecanone | 8 | 10 | 80% |
| No Compound added | — | 49 | NA |

Example 2

This example provides descriptions of compositions in use or contemplated for use in controlling plant parasitic nematodes singularly or in any combination. Table 4 provides a list of the compositions. A crop transformation base vector comprising selection expression cassettes and elements necessary for the maintenance of the plasmid in a bacterial cell is used to assemble DNA segments (promoters, leaders, introns, 3'UTR) that provide regulatory activity when operably linked to DNA segments that provide functionality in the present invention. The assembly of these DNA segments can be accomplished using methods known in the art of recombinant DNA technology. DNA coding sequences of the present invention such as any one or more of the DNA molecules identified as SEQ ID NO: 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 59, 60, and 61 are cloned and inserted into an expression cassette or inserted into operable linkage with another coding sequence or genetic element of an expression cassette. Other genetic elements can be selected and tested by those skilled in the art that provide functional expression of a methylketone in plant tissues.

TABLE 4

Descriptions of genetic elements.

| SEQ ID NO: | Name | Description |
| --- | --- | --- |
| SEQ ID NO: 1 | MKS1a | A codon-optimized polynucleotide sequence variant for *L. hirsutum* methylketone synthase |
| SEQ ID NO: 2 | MKS1b | A codon-optimized polynucleotide sequence variant for *L. hirsutum* methylketone synthase |
| SEQ ID NO: 3 | MKS1 | Amino acid sequence of the methylketone synthase protein from *L. hirsutum* |
| SEQ ID NO: 4 | LhMKS1 | Polynucleotide sequence for a codon-optimized *L. hirsutum* methylketone synthase |
| SEQ ID NO: 5 | LhMKS1 protein variant | Amino acid sequence variant of the methylketone synthase protein from *L. hirsutum* |

TABLE 4-continued

Descriptions of genetic elements.

| SEQ ID NO: | Name | Description |
|---|---|---|
| SEQ ID NO: 6 | LsMKS1 | Polynucleotide sequence for a codon-optimized *Lycopersicon esculentum* (*Solanum lycopersicum*) methylketone synthase |
| SEQ ID NO: 7 | LsMKS1 protein | Amino acid sequence of the methylketone synthase protein from *L. esculentum* |
| SEQ ID NO: 8 | AtCTP2 | A polynucleotide sequence encoding a chloroplast transit peptide from *A. thaliana* EPSPS protein |
| SEQ ID NO: 9 | AtCTP2 protein | Amino acid sequence of the chloroplast transit peptide from *A. thaliana* EPSPS protein |
| SEQ ID NO: 10 | PhCTP4 | A polynucleotide sequence encoding a chloroplast transit peptide from *Petunia hybrida* EPSPS protein |
| SEQ ID NO: 11 | PhCTP4 protein | Amino acid sequence of the chloroplast transit peptide from *Petunia hybrida* EPSPS protein |
| SEQ ID NO: 12 | CTP2-MKS1a | Polynucleotide sequence of the AtCTP2 chloroplast transit peptide fused to the MKS1a codon optimized sequence encoding methylketone synthase |
| SEQ ID NO: 13 | CTP2-MKS1a protein | Amino acid sequence of the heterologous AtCTP2-MKS1 fusion protein |
| SEQ ID NO: 14 | CTP4-MKS1a | Polynucleotide sequence of the PhCTP4 chloroplast transit peptide fused to the MKS1a codon optimized sequence encoding methylketone synthase |
| SEQ ID NO: 15 | CTP4-MKS1a protein | Amino acid sequence of the heterologous PhCTP4-MKS1a fusion protein |
| SEQ ID NO: 16 | CTP2-MKS1b | Polynucleotide sequence of the CTP2 chloroplast transit peptide fused to the MKS1b codon optimized sequence encoding methylketone synthase |
| SEQ ID NO: 17 | CTP2-MKS1b protein | Amino acid sequence of the heterologous AtCTP2-MKS1b fusion protein |
| SEQ ID NO: 18 | CTP4-MKS1b | Polynucleotide sequence of the PhCTP4 chloroplast transit peptide fused to the MKS1b codon optimized sequence encoding methylketone synthase |
| SEQ ID NO: 19 | CTP4-MKS1b protein | Amino acid sequence of the heterologous PhCTP4-MKS1b fusion protein |
| SEQ ID NO: 20 | CTP2-LhMKS1 | Polynucleotide sequence of the AtCTP2 chloroplast transit peptide fused to the LhMKS1 sequence encoding methylketone synthase |
| SEQ ID NO: 21 | CTP2-LhMKS1 protein | Amino acid sequence of the heterologous AtCTP2-LhMKS1 fusion protein |
| SEQ ID NO: 22 | CTP4-LhMKS1 | Polynucleotide sequence of the PhCTP4 chloroplast transit peptide fused to the LhMKS1 sequence encoding methylketone synthase |
| SEQ ID NO: 23 | CTP4-LhMKS1 protein | Amino acid sequence of the heterologous PhCTP4-LhMKS1 fusion protein |
| SEQ ID NO: 24 | CTP2-LsMKS1 | Polynucleotide sequence of the AtCTP2 chloroplast transit peptide fused to the LsMKS1 sequence encoding methylketone synthase |
| SEQ ID NO: 25 | CTP2-LsMKS1 protein | Amino acid sequence of the heterologous AtCTP2-LsMKS1 fusion protein |
| SEQ ID NO: 26 | CTP4-LsMKS1 | Polynucleotide sequence of the PhCTP4 chloroplast transit peptide fused to the LsMKS1 sequence encoding methylketone synthase |

TABLE 4-continued

Descriptions of genetic elements.

| SEQ ID NO: | Name | Description |
|---|---|---|
| SEQ ID NO: 27 | CTP4-LsMKS1 protein | Amino acid sequence of the heterologous PhCTP4-LsMKS1 fusion protein |
| SEQ ID NO: 28 | CTP2-MKS1a_sN | Polynucleotide sequence of the AtCTP2 chloroplast transit peptide fused to the MKS1s sequence encoding an Alanine to Serine active site variant of methylketone synthase |
| SEQ ID NO: 29 | CTP2-MKS1a_sN protein | Amino acid sequence of the AtCTP2 chloroplast transit peptide fused to the MKS1s sequence having an Alanine to Serine active site variant of methylketone synthase |
| SEQ ID NO: 30 | CTP2-MKS1a_Ad | Polynucleotide sequence of the AtCTP2 chloroplast transit peptide fused to the MKS1s sequence encoding an Asparagine to Aspartic acid active site variant of methylketone synthase |
| SEQ ID NO: 31 | CTP2-MKS1a_Ad protein | Amino acid sequence of the AtCTP2 chloroplast transit peptide fused to the MKS1s sequence having an Asparagine to Aspartic acid active site variant of methylketone synthase |
| SEQ ID NO: 32 | CTP2-MKS1a_sd | Polynucleotide sequence of the AtCTP2 chloroplast transit peptide fused to the MKS1s sequence encoding a double variant Alanine to Serine and Asparagine to Aspartic acid active site variant of methylketone synthase |
| SEQ ID NO: 33 | CTP2-MKS1a_sd protein | Amino acid sequence of the AtCTP2 chloroplast transit peptide fused to the MKS1s sequence having a double variant Alanine to Serine and Asparagine to Aspartic acid active site variant of methylketone synthase |
| SEQ ID NO: 34 | CTP2-LsMKS1_sN | Polynucleotide sequence of the AtCTP2 chloroplast transit peptide fused to the LsMKS1s sequence encoding an Alanine to Serine active site variant of methylketone synthase |
| SEQ ID NO: 35 | CTP2-LsMKS1_sN protein | Amino acid sequence of the AtCTP2 chloroplast transit peptide fused to the LsMKS1s sequence encoding an Alanine to Serine active site variant of methylketone synthase |
| SEQ ID NO: 36 | CTP2-LsMKS1_Ad | Polynucleotide sequence of the AtCTP2 chloroplast transit peptide fused to the LsMKS1s sequence encoding an Asparagine to Aspartic acid active site variant of methylketone synthase |
| SEQ ID NO: 37 | CTP2-LsMKS1_Ad protein | Amino acid sequence of the AtCTP2 chloroplast transit peptide fused to the LsMKS1s sequence encoding an Asparagine to Aspartic acid active site variant of methylketone synthase |
| SEQ ID NO: 38 | CTP2-LsMKS1_sd | Polynucleotide sequence of the AtCTP2 chloroplast transit peptide fused to the LsMKS1s sequence encoding a double variant Alanine to Serine and Asparagine to Aspartic acid active site variant of methylketone synthase |
| SEQ ID NO: 39 | CTP2-LsMKS1_sd protein | Amino acid sequence of the AtCTP2 chloroplast transit peptide fused to the LsMKS1s sequence having a double variant Alanine to Serine and Asparagine to Aspartic acid active site variant of methylketone synthase |
| SEQ ID NO: 40 | LhACP1-PI126449 | Polynucleotide sequence of an Acyl carrier protein ACP1 coding sequence from PI126449 |

TABLE 4-continued

Descriptions of genetic elements.

| SEQ ID NO: | Name | Description |
|---|---|---|
| SEQ ID NO: 41 | LhACP1-PI126449 protein | Amino acid sequence of an Acyl carrier protein ACP1 from PI126449 |
| SEQ ID NO: 42 | LhACP2-PI126449 | Polynucleotide sequence of an Acyl carrier protein ACP2 coding sequence from PI126449 |
| SEQ ID NO: 43 | LhACP2-PI126449 protein | Amino acid sequence of an Acyl carrier protein ACP2 from PI126449 |
| SEQ ID NO: 44 | LhACP1-LA1777 | Polynucleotide sequence of an Acyl carrier protein ACP1 coding sequence from LA1777 |
| SEQ ID NO: 45 | LhACP1-LA1777 protein | Amino acid sequence of an Acyl carrier protein ACP1 from LA1777 |
| SEQ ID NO: 46 | LeACP2 | Polynucleotide sequence of an Acyl carrier protein ACP2 from *L. esculentum* |
| SEQ ID NO: 47 | LeACP2 protein | Amino acid sequence of an Acyl carrier protein ACP2 from *L. esculentum* |
| SEQ ID NO: 48 | StACP2 | Polynucleotide sequence of an Acyl carrier protein ACP2 from *Solanum tuberosum* |
| SEQ ID NO: 49 | StACP2 protein | Amino acid sequence of an Acyl carrier protein ACP2 from *Solanum tuberosum* |
| SEQ ID NO: 50 | ScACP2 | Polynucleotide sequence of an Acyl carrier protein ACP2 from *Solanum chacoense* |
| SEQ ID NO: 51 | ScACP2 protein | Amino acid sequence of an Acyl carrier protein ACP2 from *Solanum chacoense* |
| SEQ ID NO: 52 | NtACP2 | Polynucleotide sequence of an Acyl carrier protein ACP2 from *Nicotiana tabacum* |
| SEQ ID NO: 53 | NtACP2 protein | Amino acid sequence of an Acyl carrier protein ACP2 from *Nicotiana tabacum* |
| SEQ ID NO: 54 | PhACP2 | Polynucleotide sequence of an Acyl carrier protein ACP2 from *Petunia hybrida* |
| SEQ ID NO: 55 | PhACP2 protein | Amino acid sequence of an Acyl carrier protein ACP2 from *Petunia hybrida* |
| SEQ ID NO: 56 | CaACP2 | Polynucleotide sequence of an Acyl carrier protein ACP2 from *Capsicum annum* |
| SEQ ID NO: 57 | CaACP2 protein | Amino acid sequence of an Acyl carrier protein ACP2 from *Capsicum annum* |
| SEQ ID NO: 58 | LeMKS1 homolog | Polynucleotide sequence of an MKS1 homolog from *L. esculentum* |
| SEQ ID NO: 59 | StMKS1 homolog | Polynucleotide sequence of an MKS1 homolog from *S. tuberosum* |
| SEQ ID NO: 60 | NtMKS1 homolog | Polynucleotide sequence of an MKS1 homolog from *N. tabacum* |
| SEQ ID NO: 61 | CaMKS1 homolog | Polynucleotide sequence of an MKS1 homolog from *C. annum* |
| SEQ ID NO: 62 | Act7 intron | 558 nucleotide actin 7 intron sequence from *A. thaliana* |

Example 3

This example describes generation of tomato or soybean transgenic hairy roots expressing MKS and the nematode infection assay. Hairy root cultures allow the rapid growth of root tissue on a large scale which can be used for testing the effectiveness of the gene of interest as set forth herein, for controlling plant parasitic nematode infestation of a crop plant. Hairy roots are characterized by fast growth, frequent branching, plagiotropism, and the ability to synthesize the same compounds as the roots of the intact plant (David et al., *Biotechnology* 2:73-76, 1984). Transfer and integration of the genes located on the root-inducing plasmid Ri of *Agrobacterium rhizogenes* into the plant genome and their expression therein (White and Nester, *J. Bacteriol.*, 141:1134-1141, 1980). These types of roots continue to grow in vitro on hormone-free medium and also exhibit a high degree of genetic stability (Aird et al., *Plant Cell Tiss. Org. Cult.* 15: 47-57, 1988). The natural ability of the soil bacterium *A. rhizogenes* to transform genes into a host plant genome results in roots being formed at the site of infection. Infection of the plant with *A. rhizogenes*, leads to the integration and expression of T-DNA in the plant genome, which causes development of a hairy root. Hairy root cultures grow rapidly, show plagiotropic root growth and are highly branched on hormone-free medium.

For soybean hairy roots, *A. rhizogenes* strain K599 is grown and maintained on LB, minimal A, or yeast extract and peptone (YEP) media. Methods for generation of transgenic tomato hairy root cultures for evaluating lesion or root knot nematodes are not significantly different other than the use of *A. rhizogenes* D1 strain. Soybean seeds are surface-sterilized by setting in chlorine gas under controlled conditions for 12-16 hours, and then aerating in a clean air hood for at least 30 minutes. Seeds are germinated in Petri dishes containing ¼ MS.

The hypocotyl or cotyledons of 6-days-old seedlings are wounded using a scalpel. The wounded cotyledons are then immersed in freshly grown *A. rhizogenes* containing the construct and subsequently vacuum infiltrated. Cotyledons are cultured under the same conditions used for seed germination with the exception that the antibiotic cefotaxime is added to the ¼ MS agar plates to prevent the *A. rhizogenes* from subsequent growth. Adventitious roots are excised from hypocotyls or cotyledons inoculated with *A. rhizogenes*. The putative transformed roots are cultured on Gamborg's B-5 agar containing 3% sucrose plus 3 g/l Gelrite, BASTA, and cefotaxime). Roots passing selection are transferred to fresh media and maintained. Cultured roots are maintained in an incubator, without light, set at 24-30° C. Roots are maintained on Gamborg's B-5 agar. A piece of root tip is excised and transferred to fresh medium every 2-4 weeks.

Following hairy root line selection, roots for the plant nematode bioassay are transferred to fresh plates containing Gamborg's B-5 medium and allowed to grow for approximately two weeks to provide sufficient tissue for nematode infection before inoculation with a mixed population of root lesion nematodes or second-stage juveniles of soybean cyst nematode (SCN) or root knot nematode (RKN). 20 plates of individual hairy root tips are placed on infection plates. 20 plates are used for testing transformed roots for reaction to lesion, SCN or RKN. Each plate contains a transformed root from a separate integration. An additional 20 plates containing a transformed lesion susceptible, SCN-susceptible or RKN-susceptible control and an additional 20 plates containing a transformed SCN-resistant or RKN-resistant control are also tested. Transformed controls are empty vectors. Plates are then inoculated with approximately 400 axenic lesion worms or 1000 sterile *H. glycines* J2s or 450 sterile *M. incognita* J2s and incubated at 26-28° C. (SCN or RKN) or 25° C. or 30° C. (lesion nematode).

Approximately six weeks after inoculation with *M. incognita* or five weeks after inoculation with *H. glycines*, infected tomato or soybean hairy roots are removed from the agar plates and the number of galls or cysts counted. For SCN hairy root plates cysts are counted directly, whereas for RKN gall numbers may be estimated. Gall scores are weighted estimates based on size. A scale is created at the beginning of scoring process. The smallest galls are given a score of 1 and as the galled areas become larger the gall score increases. The scale is then used to rate each gall on each plate in the experiment. Egg numbers are also scored at 42 days for RKN infections in tomato hairy roots. At 42 days post-infection, plates are microwaved and sieved to collect the roots. The roots are weighed, then blended in a 10% bleach solution and poured over a series of sieves to remove the root debris and collect the eggs. Eggs are removed from each plate and are counted. For lesion nematodes, plates are harvested after approximately 56 days by placing roots in glass bowls filled with sterilized water containing 50 mg/L carbenicillin and 50 mg/L kanamycin. After 9-10 days to allow the worms to exit the roots, the worms are counted under a microscope. To determine weights, root bowls are then microwaved to melt the agar and roots are collected with a sieve. The extra water is absorbed with a paper towel and the root weights recorded.

Axenic lesion, SCN and RKN larvae are prepared for use with the hairy root culture system. Axenic SCN J2s are produced as follows. Clean soybean cyst nematode eggs (i.e., eggs with soil and other debris removed) are collected and placed in a 50 ml centrifuge vial containing 30 ml of a 10% bleach solution. The bleach solution is mildly agitated and then left to settle for 2-3 minutes. The vial is mildly agitated again to re-suspend the eggs and then centrifuged for 1 minute at 1000 rpm. Under a sterile hood, the bleach solution is removed into a receptacle and 25 ml of sterile water is added into the vial of eggs. The vial is recapped under the sterile hood, mildly agitated to re-suspend the eggs and centrifuged for 1 minute at 1000 rpm. Under the sterile hood, this liquid is poured off and 25 ml of sterile water is again placed in the vial. The vial is recapped under the sterile hood and the process of agitation and centrifugation repeated. This process of washing the eggs with sterile water is repeated approximately 4 times to thoroughly rinse the bleach from the eggs. Following the last rinse under the sterile hood the liquid is removed leaving about 1-2 ml of egg concentrate. Axenic eggs are hatched by incubating them on the surface of moist filter paper resting in a solution of 5 mM zinc sulfate just deep enough to cover the surface of the filter paper. After 2-3 days J2 larvae are collected in the solution underneath the filter paper. J2s are centrifuged and further cleaned using chlorhexidine (Atkinson et al., *J. Nematol.* 28:209-215, 1996).

Axenic RKN larvae are prepared by collecting eggs by placing chopped RKN infected roots into a blender with a sufficient quantity of 10% bleach solution. The blender is pulsed on/off for 5 second intervals. This process is repeated 5-6 times. The root slurry is the passed through a series of sieves where the eggs and small debris are collected in a 500 micron sieve. Any remaining bleach solution is thoroughly rinsed from this egg/debris. Twenty milliliters of the egg/debris is added to a 50 ml conical tube and 20 ml of a 40% sucrose solution is added into the bottom of the tube, bringing the total volume to 40 milliliters. This solution is then centrifuged at 3750 rpm for 5 minutes to separate the eggs from the debris. After centrifugation, the eggs are removed and thoroughly rinsed to remove any remaining sucrose solution. Eggs are then placed into a hatch bowl containing filter paper moistened with just enough aerated tap water to cover the eggs. After 1-2 days J2 larvae are collected in the solution underneath the filter paper. J2 larvae are centrifuged and further cleaned using chlorhexidine (Atkinson et al. (1996, see above).

Axenic lesion larvae are prepared from lesion nematodes grown on corn explant plates. The nematodes are harvested by placing roots with medium onto filter paper supported by a wire sieve in a sterilized glass bowl which has been filled with sterilized water containing 50 mg/L carbenicillin and 50 mg/L kanamycin. The amount of the water is sufficient to submerge the agar, and the bowls are stored at room temperature (25° C.) for two days. The sieve is removed and the solution poured into a 50 ml conical tube, which was then centrifuged for 5 minutes at 3500×g at room temperature. After the worms settle to the bottom of the tube (further 15 minute incubation), the supernatant is decanted. Sterilized water is then added to the worm pellet containing 12 mg/L of the antifungal compound Imazilil and 50 mg/L kanamycin.

The following are results found after the transgenic expression of various combinations of promoters, transit peptides and methylketone synthase coding sequences for control of plant parasitic nematode infections in hairy roots. SCN cysts in the transgenic soybean hairy root inoculated plates are counted and the average number of cysts per replication (Rep 1 and Rep 2) tabulated. The results shown in Table 5 demonstrate that transgenic soybean roots containing the chimeric CTP-methylketone synthase coding region provides resistance to SCN infection, where all treatments having a heterologous CTP fused to a methylketone synthase show a reduction in the average cyst counts compared to the transgenic empty vector control, 4211. The constructs that lack a heterologous CTP (FMV-LsMKS1 and FMV-LhMKS1) do not show a reduction in cyst counts.

TABLE 5

Transgenic soybean roots expressing
MKS reduce SCN infection (cysts).

| | control | Test constructs | Test constructs |
|---|---|---|---|
| | D4211 | E35S-ctp2/mks1 | E35S-ctp4/mks1 |
| Rep 1 | 31.4 | 12.6 | 21.9 |
| Rep 2 | 18.3 | 9.1 | — |
| | 4211 | E35Sp-ctp2/mks1 | E35Sp-ctp4/mks1 |
| Rep 1 | 19.4 | 17.6 | 13 |
| Rep 2 | 18.4 | 11.2 | 13.7 |
| | 4211 | FMV-ctp2/LsMKS1 | E35Sp-ctp2/LsMKS1 |
| Rep 1 | 33 | 16.5 | 19.3 |
| Rep 2 | 25.4 | 15 | 22.9 |
| | 4211 | FMV-LsMKS1(no CTP) | FMV-LhMKS1 (no CTP) |
| Rep 1 | 21 | 27 | 23 |
| Rep 2 | 18 | 17 | 18 |

As can be seen in table 6 below, the expression of MKS constructs containing CTP leaders either with or without certain targeted active site mutations leads to reduction in the ability of root knot nematode to infect plants roots. In addition to the elements listed in the table above, the constructs shown contain a ~540 nucleotide actin 7 intron incorporated into the 5' untranslated region (UTR) of the fused methylketone synthase transcript and a visual fluorescent DsRED marker (driven by the FMV promoter) co-expressed in the T-DNA, downstream of the MKS open reading frame.

TABLE 6

Transgenic tomato roots expressing MKS reduce
root knot nematode infection (eggs).

| control 8221 | Test construct E35sp-ctp2/LsMKS1 | Test construct E35sp-ctp2/LsMKS1_sN | Test construct E35sp-ctp2/LsMKS1_sd |
|---|---|---|---|
| 1884.5 | 968.5 | — | 1333.4 |
| 3059.8 | 1927.4 | — | 1558 |
| 716.7 | — | 283.3 | 298.1 |

As can be seen in table 7 below, the expression of MKS constructs containing CTP leaders either with or without certain targeted active site mutations leads to reduction in the ability of root lesion nematodes to infect plants roots. In addition to the elements listed in the table above, the constructs shown contain a ~540 nucleotide actin 7 intron incorporated into the 5' untranslated region (UTR) of the fused methylketone synthase transcript and a visual fluorescent DsRED marker (driven by the FMV promoter) co-expressed in the T-DNA, downstream of the MKS open reading frame.

TABLE 7

Transgenic tomato roots expressing MKS reduce
lesion nematode infection (larvae).

| control 8221 | Test construct E35sp-ctp2/LsMKS1 | Test construct E35sp-ctp2/LsMKS1_sN | Test construct E35sp-ctp2/LsMKS1_sd |
|---|---|---|---|
| 5857.8 | 4842.4 | 3926.2 | 4897.2 |

Example 4

This example describes a plant transformation method useful in producing transgenic soybean plants and transgenic seed. Other methods are known in the art of plant cell transformation that can be applied using the DNA constructs of the present invention.

For *Agrobacterium* mediated transformation, soybean seeds are germinated overnight and the meristem explants excised (see U.S. Pat. No. 7,002,058). The meristems and the explants are placed in a wounding vessel. Soybean explants and induced *Agrobacterium* cells from a strain containing plasmid DNA with the expression cassettes of the present invention and a plant selectable marker cassette are mixed within about 14 hours from the time of initiation of seed germination and wounded using sonication. Following wounding, explants are placed in co-culture for 2-5 days at which point they are transferred to selection media for 6-8 weeks to allow selection and growth of transgenic shoots. Trait positive shoots are harvested after approximately 6-8 weeks and placed into selective rooting media for 2-3 weeks. Shoots producing roots are transferred to the greenhouse and potted in soil. Shoots that remain healthy on selection but that do not produce roots are transferred to non-selective rooting media for an additional two weeks. Roots from any shoots that produce roots off selection are tested for expression of the plant selectable marker before they are transferred to the greenhouse and potted in soil. Additionally, a DNA construct can be transferred into the genome of a soybean cell by particle bombardment and the cell regenerated into a fertile soybean plant as described in U.S. Pat. No. 5,015,580.

Transgenic soybean plant cells are transformed with recombinant DNA of this invention. Progeny transgenic plants and seed of the transformed plant cells are selected that provide pest resistance, especially nematode resistance.

Example 5

A soybean cyst nematode pot assay is used to evaluate the resistance of transgenic soybean plants comprising the methylketone synthase coding sequence to infection by and reproduction of the soybean cyst nematode (*Heterodera glycines*) on roots. Three or four inch diameter square pots are filled with clean sand and watered thoroughly. Transgenic and control soybean seeds, or alternatively any rooted plant parts, are planted one per pot in the center of the pot and watered well to remove air pockets. The pots are incubated in the greenhouse or growth chamber at 20° C. to 30° C. until the plants reached a suitable age for inoculation. Soybeans started from seed are typically inoculated 2-3 weeks after planting, while transplants are inoculated 1-3 days after planting. The test inoculum consists of eggs from ripe *H. glycines* cysts collected from the soil and roots of infested soybean plants. A 250 micron mesh sieve is used to collect the cysts, which are then crushed in a Tenbroeck glass tissue homogenizer to release the eggs. The eggs are further purified by sieving and centrifugation over 40 percent sucrose solution at 4000 RPM for 5 minutes. Inoculum for an experiment consisted of water containing 500 vermiform eggs per mL. Five mL of the egg suspension is applied over the surface of the sand containing the test plants and the eggs are lightly watered in. The test plants are then returned to the greenhouse or growth chamber and incubated for 3-4 weeks to allow for root infection and cyst formation. The roots are then harvested by gently removing the pot and sand and rinsing in water. The severity of nematode infection is measured by counting the number of nematode cysts adhering to the root system. Alternatively, the sand and roots could be diluted in water and passed over a 250 micron sieve to collect and concentrate the cysts for storage or counting.

Example 6

This example describes the detection and measurement of the recombinant DNA construct in the transgenic plant cell. Detecting or measuring transcription of the recombinant DNA construct in the transgenic plant cell of the invention can be achieved by any suitable method, including protein detection methods (for example, western blots, ELISAs, and other immunochemical methods), measurements of enzymatic activity, or nucleic acid detection methods (for example, Southern blots, northern blots, PCR, RT-PCR, fluorescent in situ hybridization). Such methods are well known to those of ordinary skill in the art as evidenced by the numerous handbooks available; see, for example, Joseph Sambrook and David W. Russell, "Molecular Cloning: A Laboratory Manual" (third edition), Cold Spring Harbor Laboratory Press, NY, 2001; Frederick M. Ausubel et al. (editors) "Short Protocols in Molecular Biology" (fifth edition), John Wiley and Sons, 2002; John M. Walker (editor) "Protein Protocols Handbook" (second edition), Humana Press, 2002; and Leandro Peña (editor) "Transgenic Plants: Methods and Protocols", Humana Press, 2004.

DNA sequence information provided by the invention allows for the preparation of relatively short DNA (or RNA) sequences having the ability to specifically hybridize to DNA sequences of the selected polynucleotides disclosed herein. The polynucleotides disclosed in the present invention include SEQ ID NO: 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 59, 60, and 61. In these aspects, nucleic acid probes of an appropriate length are prepared. The ability of the nucleic acid probes to specifically hybridize to one or more of these gene coding sequences lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a portion of a polynucleotide sequence of the present invention to be homologous or complementary to the sequence for use in detecting, amplifying a defined polynucleotide segment using PCR™ technology (A Guide to Methods and Applications, Academic Press: San Diego, 1990). PCR primer pairs can be derived from a known sequence, for example, by using computer programs intended for that purpose such as Primer (Version 0.5© (1991, Whitehead Institute for Biomedical Research, Cambridge, Mass.). Primers and probes based on the sequences disclosed herein can be used to confirm and, if necessary, to modify the disclosed sequences by conventional methods, for example, by re-cloning and re-sequencing. Exemplary PCR reaction conditions may include: Component Amount/Volume required sub-library aliquot 1 μl Gene-specific primer 1, 1 μl (100 pmol, GenomeWalker™) Adaptor primer 1 (AP1), 1 μl dNTP mix (10 mM of each dNTP), 1 μl DMSO 2.5 μl (or 2-5% final concentration) 10×PCR buffer, 5 μl (final concentration of 1×) Amplitaq Gold™, 0.5 μl distilled water for final reaction volume of 50 μl reaction conditions for primary PCR:

A. 9 minutes at 95° C.;
B. 94° C. for 2 seconds, 70° C. for 3 minutes; repeat 94° C./70° C. cycling for total of 7 times;
C. 94° C. for 2 seconds, 65° C. for 3 minutes; repeat 94° C./65° C. cycling for total of 36 times;
D. 65° C. for 4 minutes as a final extension;
E. 10° C. for an extended incubation NESTED PCR (secondary PCR reaction) Component Amount/Volume Required 1:50 dilution of the primary PCR reaction; 1 μl Gene-specific primer 2; 1 μl (100 pmol, GenomeWalker™ Adaptor primer 2; 1 μl or 3 (AP2 or AP3), dNTP mix (10 mM of each dNTP); 1 μl DMSO; 2.5 μl 10×PCR buffer containing $MgCl_2$; 5 μl (final concentration of 1×) Amplitaq Gold™; 0.5 μl distilled water to final reaction volume of 50 μl reaction. Conditions for Nested PCR:

A. 9 minutes at 95° C.;
B. 94° C. for 2 seconds, 70° C. for 3 minutes; repeat 94° C./70° C. cycling for total of 5 times;
C. 94° C. for 2 seconds, 65° C. for 3 minutes; repeat 94° C./65° C. cycling for total of 24 times;
D. 65° C. for 4 minutes as a final extension;
E. 10° C. for an extended incubation.

PCR conditions can be modified from the described conditions by those skilled in the method to produce an amplicon.

Detection of foreign gene expression in transgenic plant is monitored by an immunological method for example ELISA (enzyme-linked immunosorbent assays) for a quantitative determination of the level of corresponding protein obtained. Quantitative determination of the encoded protein in the leaves of transgenic plants is performed using ELISA, for example as disclosed in Clark et al.: ELISA Techniques. In: Weissbach A, Weissbach H (eds) *Methods in Enzymology* 118:742-766, Academic Press, Florida (1986).

All publications and patents referenced herein are intended to be herein incorporated by reference in their entirety.

The invention claimed is:

1. A polynucleotide comprising a sequence encoding a polypeptide comprising a plant methylketone synthase and a heterologous transit peptide operably linked to the plant methylketone synthase, wherein the polypeptide has at least 95% identity to SEQ ID NO:25, and wherein the polypeptide has methylketone synthase activity.

2. The polynucleotide of claim 1, wherein the transit peptide is a chloroplast transit peptide.

3. The polynucleotide of claim 2, wherein the chloroplast transit peptide is selected from the group consisting of an EPSPS chloroplast transit peptide, a small subunit ribulose-1,5-bisphosphate carboxylase chloroplast transit peptide, a ferredoxin chloroplast transit peptide, a ferredoxin oxidoreductase chloroplast transit peptide, a light-harvesting complex protein I and protein II chloroplast transit peptide, and a thioredoxin F chloroplast transit peptide.

4. The polynucleotide of claim 1, wherein the sequence encoding the polypeptide exhibits at least 95% sequence identity to SEQ ID NO:24.

5. A construct comprising the polynucleotide of claim 1 operably linked to a promoter functional in plants.

6. A plant cell comprising the polynucleotide of claim 1.

7. The plant cell of claim 6, wherein the transit peptide is a chloroplast transit peptide.

8. The plant cell of claim 6, wherein said plant cell is from a seed, root, leaf, shoot, flower, pollen, or ovule.

9. The plant cell of claim 6, wherein said cell produces a methylketone.

10. The plant cell of claim 9, wherein said methylketone is 2-undecanone, 2-tridecanone, or 2-pentadecanone.

11. The plant cell of claim 6, wherein said cell is a crop plant cell.

12. The plant cell of claim 6, wherein said cell is from a plant selected from the group selected from cotton, soybean, canola, corn, wheat, rice, sunflower, sorghum, sugarcane, potato, tomato, and a tree.

13. A plant or a part thereof comprising the polynucleotide of claim 1.

14. The plant or part thereof of claim 13, wherein the part thereof is selected from the group consisting of a seed, pollen, a root, a leaf, a shoot, a flower and an ovule.

15. A processed product comprising a plant tissue comprising the polynucleotide of claim 1.

16. The processed product of claim 15, selected from the group consisting of meal, flour, oil, hay, starch, juice, protein extract, and fiber.

17. A method for controlling a pathogen or pest in a plant comprising expressing in the plant the construct of claim 5.

18. The method for controlling a pathogen or pest in a plant of claim 17, wherein the polynucleotide sequence comprises a sequence that encodes a second heterologous transit peptide operably linked to a sequence that encodes an acyl carrier protein.

19. The method of claim 18, wherein the pathogen or pest is a nematode.

20. The method of claim 19, wherein the nematode is selected from the group consisting of *Heterodera* species, *Globodera* species, *Meloidogyne* species, *Rotylenchulus* species, *Hoplolaimus* species, *Belonolaimus* species, *Pratylenchus* species, *Longidorus* species, *Paratrichodorus* species, *Ditylenchus* species, *Xiphinema* species, *Dolichodorus* species, *Helicotylenchus* species, *Radopholus* species, *Hirschmanniella* species, *Tylenchorhynchus* species, and *Trichodorus* species.

21. The method of claim 18, wherein the pathogen or pest is an insect pest.

22. The method of claim 21, wherein the insect pest is selected from the group consisting of *Diabrotica, Diaprepes, Pachnaeus, Asynonychus, Lycoriella, Sciara, Stenophlus*, and *Bradysia*.

23. A method of producing seed, comprising crossing the plant of claim 13 with itself or a second plant.

24. The method of producing seed of claim 23, wherein the polynucleotide sequence comprises a sequence that encodes a second heterologous transit peptide operably linked to a sequence that encodes an acyl carrier protein.

25. The polynucleotide of claim 1, further comprising a sequence that encodes a second heterologous transit peptide operably linked to a sequence that encodes an acyl carrier protein.

26. The polynucleotide of claim 25, wherein said sequence that encodes a second heterologous transit peptide operably linked to a sequence that encodes an acyl carrier protein encodes a polypeptide that comprises an amino acid sequence exhibiting at least 95% identity to a polypeptide selected from the group consisting of SEQ ID NO: 41, 43, 45, 47, 49, 51, 53, 55, and 57.

27. The polynucleotide of claim 25, wherein said second transit peptide is a chloroplast transit peptide.

28. The polynucleotide of claim 25, wherein said second transit peptide is selected from the group consisting of an EPSPS chloroplast transit peptide, a small subunit ribulose-1,5-bisphosphate carboxylase chloroplast transit peptide, a ferredoxin chloroplast transit peptide, a ferredoxin oxidoreductase chloroplast transit peptide, a light-harvesting complex protein I and protein II chloroplast transit peptide, and a thioredoxin F chloroplast transit peptide.

29. The polynucleotide of claim 25, wherein said sequence that encodes a second heterologous transit peptide operably linked to a sequence that encodes an acyl carrier protein exhibits at least 95% sequence identity to a polynucleotide sequence selected from the group consisting of SEQ ID NO: 40, 42, 44, 46, 48, 50, 52, 54, and 56.

30. The plant cell of claim 6, wherein the polynucleotide sequence comprises a sequence that encodes a second heterologous transit peptide operably linked to a sequence that encodes an acyl carrier protein.

31. The plant or part thereof of claim 13, wherein the polynucleotide sequence comprises a sequence that encodes a second heterologous transit peptide operably linked to a sequence that encodes an acyl carrier protein.

32. A processed product of a plant, plant part, seed or progeny, wherein the product comprises the plant cell of claim 6.

33. The processed product of claim 32, wherein the processed product is selected from the group consisting of meal, flour, oil, hay, starch, juice, protein extract, and fiber.

34. The polynucleotide of claim 1, wherein the polypeptide comprises an amino acid sequence with at least 98% identity to SEQ ID NO:25.

* * * * *